(12) United States Patent
Ranish et al.

(10) Patent No.: US 8,535,948 B2
(45) Date of Patent: Sep. 17, 2013

(54) METHOD TO DETERMINE PROTEIN INTERACTION SITES

(75) Inventors: Jeff Ranish, Seattle, WA (US); Jie Luo, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 509 days.

(21) Appl. No.: 12/748,289

(22) Filed: Mar. 26, 2010

(65) Prior Publication Data
US 2010/0248261 A1 Sep. 30, 2010

Related U.S. Application Data

(60) Provisional application No. 61/163,805, filed on Mar. 26, 2009.

(51) Int. Cl.
*G01N 24/00* (2006.01)
*G01N 33/534* (2006.01)
*G01N 33/53* (2006.01)

(52) U.S. Cl.
USPC ............... 436/173; 436/544; 435/7.5

(58) Field of Classification Search
None
See application file for complete search history.

(56) References Cited

U.S. PATENT DOCUMENTS

| 5,306,809 | A | | 4/1994 | Boon et al. |
| 5,976,857 | A | * | 11/1999 | Powell et al. ............ 435/207 |
| 2009/0062478 | A1 | | 3/2009 | Carrillo et al. |

OTHER PUBLICATIONS

Trester-Zedlitz et al. A modular cross-linking approach for exploring protein interactions. J. Am. Chem. Soc. 2003, vol. 125, pp. 2416-2425.*
Chowdhury et al., Anal. Chem. (2006) 78:8183-8193.
Lu et al., Anal. Chem. (2008) 80:9279-9281.
Soderblom et al., Rapid Commun. Mass Spectrom. (2007) 21:3395-3408.
International Search Report for PCT/US10/28931, mailed on May 18, 2010, 1 page.
Written Opinion of the International Searching Authority for PCT/US10/28931, mailed on May 18, 2010, 5 pages.

* cited by examiner

*Primary Examiner* — Shafiqul Haq
(74) *Attorney, Agent, or Firm* — Morrison & Foerster LLP

(57) ABSTRACT

The invention provides improved crosslinkers which permit more efficient determination of protein interactions in biological samples.

17 Claims, 19 Drawing Sheets

MW: 1752.7117 Da
Reporter Mass: 1752.7117 − 2(214.0590) = 1324.5937 Da
Linker Arm: ($C_4H_6O_2N_1$) = 100.0399 Da

PIR-3

MW: 1039.4287 Da
Reporter Mass: 1039.4287 − 2(242.0903) = 555.2481 Da
Linker Arm: $(C_4H_{10}O_2N_1) = 128.0712$ Da Chemical Formula: $C_{45}H_{39}F_{10}N_5O_{11}S$
Exact Mass: 1047.22
Molecular Weight: 1047.87
Structure of the BDRG Crosslinker

Examples of crosslink peptides from the beta-lactoglobulin

Peptide 1
K.TK[468.17]IPAVFK.I
K.ALK[468.17]ALPMHIR.L
R.TPEVDDEALEK[468.17]FDK.A
K.TK[468.17]IPAVFK.I
K.ALK[468.17]ALPMHIR.L
K.IPAVFK[468.17]IDALNENK.V
K.IDALNENK468.67VLVLDTDYK.K
R.TPEVDDEALEK[468.17]FDK.A
K.IPAVFK[468.17]IDALNENK.V
K.VLVLDTDYK[468.17]K.Y
K.ALK[468.17]ALPMHIR.L
K.ALK[468.17]ALPMHIR.L Peptide 2
K.IDALNENK468.67VLVLDTDYK.K
K.IDALNENK468.67VLVLDTDYK.K
K.IDALNENK468.67VLVLDTDYK.K
A.LIVTQTM[147.19]K[468.17]GLDIQK.V
A.LIVTQTM[147.19]K[468.17]GLDIQK.V
A.LIVTQTMK[468.17]GLDIQK.V
A.LIVTQTMK[468.17]GLDIQK.V
A.LIVTQTMK[468.17]GLDIQK.V
R.TPEVDDEALEK[468.17]FDK.A
R.TPEVDDEALEK[468.17]FDK.A
K.IPAVFK[468.17]IDALNENK.V
R.TPEVDDEALEK[468.17]FDK.A

FIG. 5

*Location of Crosslinked Lysine Residues on the Structure of Beta-Lactoglobulin (1bsy)*

Mapping of a Subset of BDRG Crosslinks onto the Structure of Pol II

SEQUENCE LISTING

```
<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: synthetic construct

<400> SEQUENCE: 1

Lys Thr Lys Pro Ala Val Phe Lys
1               5

<210> SEQ ID NO 2
<211> LENGTH: 10
```

```
<212> TYPE: PRT
<213> ORGANISM: Artificial Sequence
<220> FEATURE:
<223> OTHER INFORMATION: synthetic construct

<400> SEQUENCE: 2

Lys Thr Lys Ile Pro Ala Val Phe Lys Ile
1               5                   10

<210> SEQ ID NO 3
<211> LENGTH: 19
<212> TYPE: PRT
<213> ORGANISM: Artificial Sequence
<220> FEATURE:
<223> OTHER INFORMATION: synthetic construct

<400> SEQUENCE: 3

Lys Ile Asp Ala Leu Asn Glu Asn Lys Val Leu Val Leu Asp Thr Asp
1               5                   10                  15

Tyr Lys Lys

<210> SEQ ID NO 4
<211> LENGTH: 12
<212> TYPE: PRT
<213> ORGANISM: Artificial Sequence
<220> FEATURE:
<223> OTHER INFORMATION: synthetic construct

<400> SEQUENCE: 4

Lys Ala Leu Lys Ala Leu Pro Met His Ile Arg Leu
1               5                   10

<210> SEQ ID NO 5
<211> LENGTH: 16
<212> TYPE: PRT
<213> ORGANISM: Artificial Sequence
<220> FEATURE:
<223> OTHER INFORMATION: synthetic construct

<400> SEQUENCE: 5

Arg Thr Pro Glu Val Asp Asp Glu Ala Leu Glu Lys Phe Asp Lys Ala
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic construct

<400> SEQUENCE: 6

Ala Leu Ile Val Thr Gln Thr Met Lys Gly Leu Asp Ile Gln Lys Val
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetic construct

<400> SEQUENCE: 7

Lys Ile Pro Ala Val Phe Lys Ile Asp Ala Leu Asn Glu Asn Lys Val
1               5                   10                  15

<210> SEQ ID NO 8
<211> LENGTH: 16
```

```
<212> TYPE: PRT
<213> ORGANISM: Artificial Sequence
<220> FEATURE:
<223> OTHER INFORMATION: synthetic construct

<400> SEQUENCE: 8

Ala Leu Ile Val Thr Gln Thr Met Lys Gly Leu Asp Ile Gln Lys Val
 1               5                  10                  15

<210> SEQ ID NO 9
<211> LENGTH: 12
<212> TYPE: PRT
<213> ORGANISM: Artificial Sequence
<220> FEATURE:
<223> OTHER INFORMATION: synthetic construct

<400> SEQUENCE: 9

Lys Val Leu Val Leu Asp Thr Asp Tyr Lys Lys Tyr
 1               5                  10

<210> SEQ ID NO 10
<211> LENGTH: 20
<212> TYPE: PRT
<213> ORGANISM: Artificial Sequence
<220> FEATURE:
<223> OTHER INFORMATION: synthetic construct

<400> SEQUENCE: 10

Lys Leu Gln Asp Leu Gly Leu Lys Pro Ala Ser Val Asp Pro Ala Thr
 1               5                  10                  15

Ile Lys Arg Gln
            20

<210> SEQ ID NO 11
<211> LENGTH: 16
<212> TYPE: PRT
<213> ORGANISM: Artificial Sequence
<220> FEATURE:
<223> OTHER INFORMATION: synthetic construct

<400> SEQUENCE: 11

Arg Leu Met Asp Gln Ile Gln Pro Ile Ile Asp Ser Leu Lys Lys Ile
 1               5                  10                  15

<210> SEQ ID NO 12
<211> LENGTH: 7
<212> TYPE: PRT
<213> ORGANISM: Artificial Sequence
<220> FEATURE:
<223> OTHER INFORMATION: synthetic construct

<400> SEQUENCE: 12

Asn Pro Leu Glu Lys Arg Asp
 1               5
```

METHOD TO DETERMINE PROTEIN INTERACTION SITES

CROSS-REFERENCE TO RELATED APPLICATIONS

This application claims priority from U.S. provisional application 61/163,805 filed Mar. 26, 2009. The contents of this document are incorporated herein by reference.

STATEMENT OF RIGHTS TO INVENTIONS MADE UNDER FEDERALLY SPONSORED RESEARCH

This work was supported in part by grant number P50 GM076547 from the National Institutes of Health. The U.S. government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 655652000100Seqlist.txt | May 7, 2010 | 3,002 bytes |

TECHNICAL FIELD

The invention relates to methods to determine the proteins participating in complex interactions and in determining the structural features of the complex. More specifically, the invention concerns crosslinking agents that permit improved results employing these techniques.

BACKGROUND ART

Systems biology is concerned with elucidating interaction networks that underlie cellular functions, in particular, interactions of proteins. Identification of which proteins interact in, for example, a signaling pathway, provides information that can lead to strategies for controlling such pathways. Thus, knowledge that protein A interacts with protein B opens the possibility of controlling the action of protein B by targeting protein A. Further, understanding the structural features of the interacting proteins as they relate to each other provides information useful in the design of small molecules that might interfere with, or encourage, the interaction, as well as diagnostic tools for understanding mutations in the protein and sequences that may interfere with, or encourage, such interactions.

Multiple approaches have been used to study such interactions, including X-ray crystallography, and nuclear magnetic resonance (NMR) spectroscopy. Other methods used to identify interacting proteins include the yeast-two-hybrid method and in vitro binding assays with purified proteins. In addition, affinity purification of the complexes combined with mass spectrometry (MS) of the complex itself has been used. None of these methods, however, is sufficiently convenient and informative to provide satisfactory data.

Chowdhury, S. M., et al., *Anal. Chem.* (2006) 78:8183-8193, which is incorporated herein by reference, provide a general description of a particularly useful MS method and describe several crosslinking agents that may be employed. In brief, this method is applied either to a purified complex or to a more crude extract of cellular material and employs crosslinking agents that are able to link amino acid chains that contain functional groups—i.e., amines or sulfhydryl groups—that are reactive with functional groups at each end of a bifunctional linking moiety. Typically, the proximity of these groups either on the same protein chain or on chains of different proteins is less than 100 Å. After the above-mentioned functional groups in sufficient proximity have been chemically crosslinked, the proteins are treated with proteases, typically trypsin. Trypsin reduces the size of the peptides at either end of the crosslinker, which is favorable for subsequent MS analysis. The crosslinkers employed by Chowdhury also contain a chemical moiety separating the two reactive groups that contains a bond that is particularly labile during MS analysis. In addition, the crosslinkers contain a biotin residue that permits affinity purification of the crosslinked and trypsin-treated peptides. The resulting isolated crosslinked peptides are then subjected to MS analysis.

In Chowdhury's method, after biotin affinity enrichment, the majority of the ions detected by MS will be crosslinker-modified peptides, including monolinks, crosslinks, and looplinks. Monolinks usually predominate. Crosslinker-modified peptides are isolated and subjected to collision induced dissociation (CID) conditions that effect cleavage of the crosslinker at the cleavage site. In CID, the isolated peptide ion is collided with inert gas (such as argon), resulting in fragmentation of the peptide at MS labile bond. In the case of an interpeptide crosslink, the CID liberates the two peptides coupled to portions of the crosslinker as well as a reporter molecule derived from the crosslinker. A mass spectrum of the components is obtained. The individual peptide-containing components are then subjected to further fragmentation by CID to obtain characteristic mass spectra, which can be interpreted by database search algorithms to identify the amino acid sequence of the peptides associated with the remains of the crosslinker. Because databases are available to associate sequences with known proteins, identification of the individual peptides associated with the crosslinker is often sufficient to permit identification of the linked proteins. The location of the site of cros slinking is determined directly from the MS fragmentation spectrum of the peptide.

Other crosslinkers used in this general method are described in Lu, Y., et al., *Anal. Chem.* (2008) 80:9279-9281 and Soderblom, E. J., et al., *Rapid Commun. Mass Spectrom.* (2007) 21:3395-3408, and those shown in FIG. 1A.

SUMMARY OF THE INVENTION

The present invention employs new crosslinkers with superior properties. The crosslinkers of the invention have only a single site cleavable under low energy MS/MS conditions, thus eliminating the complicating factor of a separate reporter ion. In Chowdhury's approach, the separate reporter ion helps distinguish different types of crosslinked peptides. In contrast, the present method determines the crosslink type from the mass difference of the parental ion in the first mass spectrum obtained (MS1) and the daughter ions in the spectrum taken after the crosslinker has been cleaved (MS2), and the appearance (or not) of an intrinsic reporter—a portion of the crosslinker. The mass spectrometer is programmed to acquire two additional spectra, one for each of the daughter ions. These tertiary spectra (MS3) are produced by isolation and fragmentation of each daughter ion, and permit identification of the peptide sequences by database searching.

Thus, in one aspect, the invention is directed to a crosslinker which comprises two protein-reactive groups, each linked through a spacer moiety to a single, low energy MS labile bond, wherein at least one of said spacers is substituted with an affinity ligand to permit purification of crosslinker-modified peptides, including cros slinks, monolinks, and looplinks. Upon reaction with target protein(s), the crosslinkers may form a crosslink, in which both ends of the crosslinker react with functional groups in the target protein(s), or a monolink, in which only one end of the crosslinker has reacted with a functional group in the target protein(s). If a crosslink resides within one peptide after proteolysis, it is called a looplink.

The crosslinkers of the invention are represented by Formula I:

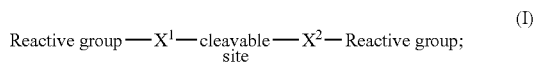

$$\text{Reactive group} - X^1 - \underset{\text{site}}{\text{cleavable}} - X^2 - \text{Reactive group;}  \quad (I)$$

wherein each of $X^1$ and $X^2$ is independently a branched or linear spacer moiety comprising 2-10 atom members selected from the group consisting of carbon, nitrogen, sulfur, and oxygen, wherein each carbon atom is optionally substituted with =O;

wherein at least one of $X^1$ and $X^2$ is substituted by an "affinity ligand" that is a moiety having specific affinity for a binding partner;

wherein each "reactive group" is independently a group that reacts with an amine, hydroxyl, sulfhydryl, or carboxyl group of a protein to form a covalent bond with the protein; and wherein the "cleavable site" is an MS cleavable linker which comprises a single low energy MS labile bond.

In a further aspect, the invention is directed to a method of identifying proteins associated with each other in a sample or single proteins which are self-associated as well as the structural parameters of such proteins by identifying the sites of proximity using the crosslinkers of the invention. These "complexed proteins" and the location of proximal lysine residues in a sample containing said proteins are identified by treating said sample with a crosslinker as described herein to obtain a mixture of crosslinker-modified proteins. Such a method may further comprise: treating the mixture of crosslinker-modified proteins with a protease to obtain digested crosslinker-modified peptides; purifying the digested crosslinker-modified peptides to separate crosslinker-modified peptides from unmodified peptides; and obtaining mass spectra of the crosslinker-modified peptides as well as mass spectra of fragmentation products derived from the crosslinker-modified peptides.

BRIEF DESCRIPTION OF THE DRAWINGS

FIGS. 1A-1 shows the crosslinker PIR (protein interaction reporter)-1, with a molecular weight of 1752.7117 Daltons. FIG. 1A-2 shows the crosslinker PIR-2, with a molecular weight of 2032.8176 Daltons. FIG. 1A-3 shows crosslinker PIR-3, with a molecular weight of 1039.4387 Daltons. See, for example, Zhang et al. *Mol. Cell. Proteomics* 2009, 8(3), 409-420.

FIG. 1B depicts the "BDRG crosslinker," which comprises a biotin-aspartic acid-RINK-glycine-glycine framework with pentafluorophenol reactive groups. FIG. 1C depicts a crosslinker with a BDRGD (biotin-aspartic acid-RINK-glycine-aspartic acid) framework and N-hydroxysuccinimide reactive groups. FIG. 1D shows a crosslinker with glycine-RINK-cysteine-succinic acid-t-butyldisulfide ("GRCSS") framework, with N-hydroxysuccinimide reactive groups.

FIGS. 2A, 2B and 3 are schematics showing the method for identifying subject peptides.

FIG. 5 shows the crosslinked peptides (SEQ ID NOS:2-9) obtained from β-lactoglobulin using the method of the invention. The number shown in brackets in each sequence indicates the molecular weight of the lysine residue modified by the mass of the BD or RG moiety derived from the BDRG crosslinker. The R., K. or alanine (A.) in each peptide sequence is followed by the residue immediately downstream of the arginine, lysine or alanine in the protein from which the peptide was derived. In cases where an A is shown followed by a dot, the known sequence of the protein indicates that an alanine actually precedes the detected peptide in the intact protein. While it is expected that peptides derived from tryptic cleavage will have K or R preceding the first amino acid in the intact protein sequence, this is not always the case. Non-specific tryptic cleavage or cleavage by an endogenous protease could produce peptides that do not have K or R preceding the first amino acid in the intact protein sequence.

DETAILED DESCRIPTION OF THE INVENTION

Figure 1A:
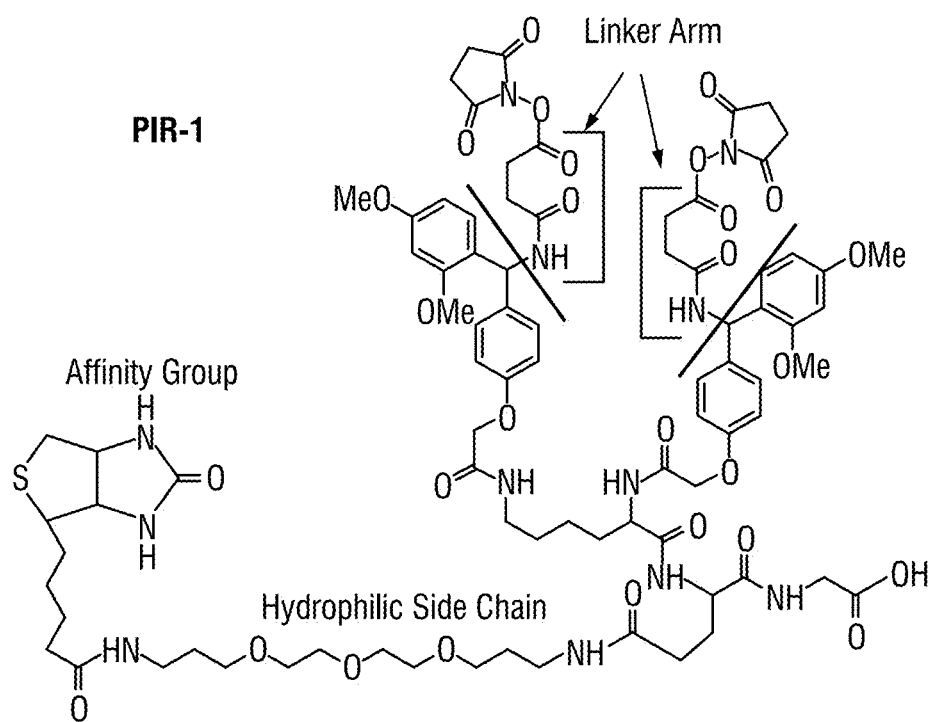
FIG. 1A depicts some of the crosslinkers known in the prior art.
Figures 1, 1A, 2:
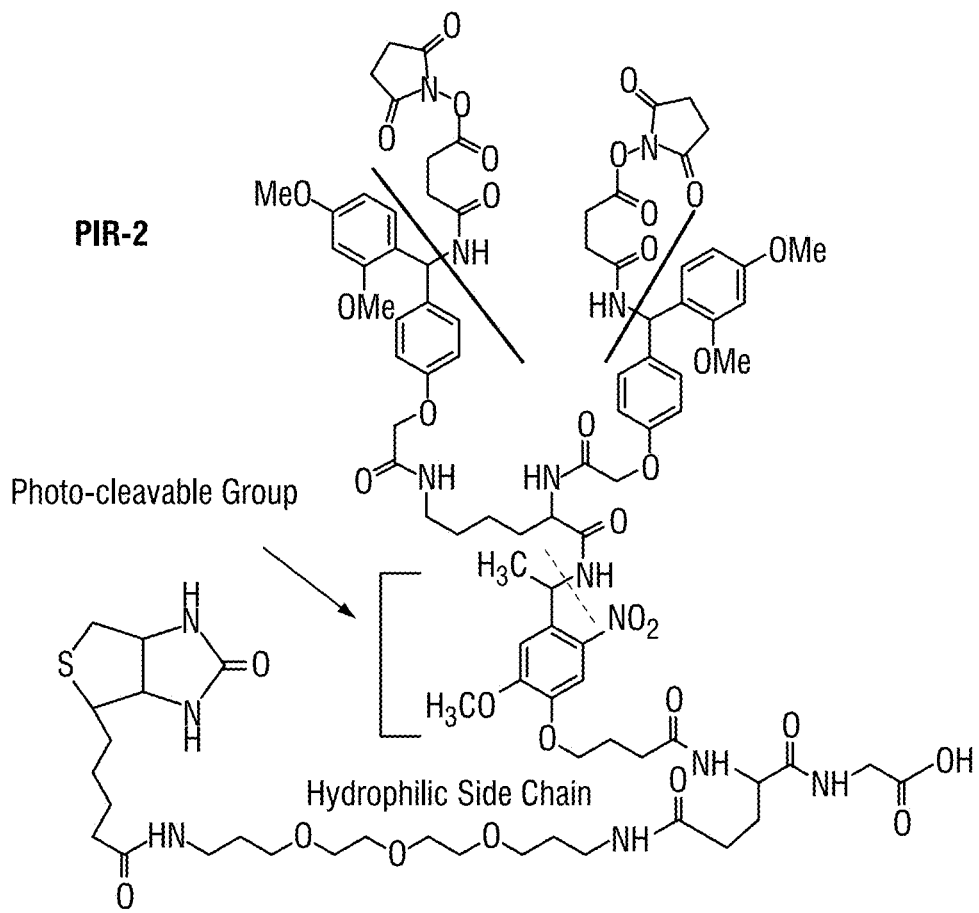

Thus, in one aspect, the invention is directed to a crosslinker which comprises two reactive groups which are leaving groups reactive to amine, hydroxyl, sulfhydryl, or carboxyl groups on a test protein, wherein the reactive groups are linked through spacer moieties to a single MS labile bond, wherein at least one of said spacer moieties is substituted with an affinity ligand to permit purification of crosslinker-modified peptides.

Reactive groups include any group which is displaced by an amino acid substituent in a test protein to yield a covalent bond with the crosslinker molecule. It will be recognized by one of skill in the art that certain reactive groups are reactive only if connected to a spacer through an activating chemical moiety. For example, pentafluorophenol and N-hydroxysuccinimide are good leaving groups, but are reactive to amines when they are part of an ester moiety. Thus, such leaving groups should be connected to a terminal carbonyl of a spacer to form a reactive pentafluorophenyl or N-succinimidyl ester.

Suitable reactive groups are known in the art and include, for example, pentafluorophenol and structural variants thereof (react with amines), N-hydroxysuccinimide and structural variants thereof (react with amines), aryl azides (react with primary amines), carbodiimides (react with amines or carboxyls), hydrazides (react with modified carbohydrates), hydroxymethyl phospines (react with amines), imidoesters (react with amines), isocyanates (react with hydroxyls), maleimides (react with sulfhydryls), vinyl sulfones (react with sulfhydryls, amines, and hydroxyls), and pyridyl disulfides (react with sulfhydryls). The reactive groups in Formula (I) may be the same or different.

In preferred embodiments, the reactive groups are reactive to amine groups on a test protein. In further preferred embodiments, the reactive groups are independently pentafluorophenol, N-hydroxysuccinimide (NHS), N-hydroxysulfosuccinimide (sulfo-NHS), or 4-sulfotetrafluorophenol (STP). In still further preferred embodiments, the reactive groups are independently pentafluorophenol or N-hydroxysuccinimide (NHS). Pentafluorophenol is particularly preferred, as the corresponding esters react more efficiently with amines and have lower rates of hydrolysis than commonly used NHS-derived esters, improving the crosslinking efficiency. N-hydroxysulfosuccinimide and 4-sulfotetrafluorophenol are preferred leaving groups because they are easily dissolved in water.

In a detailed aspect, the crosslinkers of the invention are of the Formula (I), wherein the reactive groups are each independently $R^1$—O—, wherein each $R^1$ is independently pentafluorophenyl, N-succinimidyl, N-sulfosuccinimidyl, or 4-sulfotetrafluorophenyl, and wherein each $R^1$—O— group is connected to a carbonyl group of $X^1$ or $X^2$ to form an ester, and is displaceable by the nitrogen of protein amino group of a test protein, and wherein $X^1$, $X^2$, and the cleavable site are defined as for formula (3). In preferred embodiments, each $R^1$ is independently pentafluorophenyl or N-succinimidyl.

The cleavage site comprises a low energy MS cleavable bond. Suitable moieties with low energy MS cleavable bonds are known in the art. In preferred embodiments, the cleavage site is moiety of formula (1), wherein R is H or alkyl $C_{1-6}$:

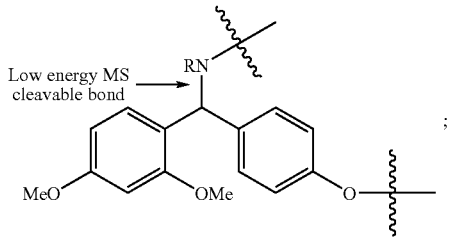

a moiety of formula (2), wherein R is H or alkyl $C_{1-6}$:

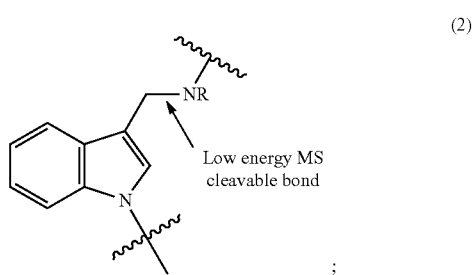

or a moiety of formula (3):

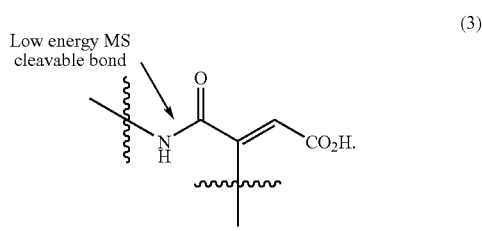 [SMILES: *NC(=O)/C(*)=C/C(=O)O]

In further preferred embodiments, the cleavage site is a moiety of formula (1) or formula (2), wherein R is H or alkyl $C_{1-6}$ in each case. In still further preferred embodiments, the cleavage site is a moiety of formula (1), where R is H or alkyl $C_{1-6}$.

The affinity ligand is a ligand which enables purification of the crosslinker-modified peptides to remove peptide fragments which have no affinity ligand attached. A suitable ligand may be biotin, as illustrated in the BDRG framework, or may be other receptor ligands wherein the corresponding receptor acts as the binding partner for affinity purification. For example, alternative ligands include desthiobiotin (streptavidin receptor) or fluorinated moieties which could be purified using fluorous solid phase extraction. Exemplary fluorinated moieties are perfluorocarbon alkyl chains of varying lengths, such as —$C_6F_{13}$ or —$C_8F_{17}$. Other suitable affinity ligands include moieties containing a disulfide bond, such as t-butyl disulfide, or S-acetylthioacetate group. After reducing the disulfide bond or deprotecting the thioacetyl group with hydroxylamine, the resulting sulfhydryl groups can be captured with sulfhydryl capture reagents such as iodoacetamide derivatives or dipyridyl disulfide derivatives. In preferred embodiments, the affinity ligand is biotin.

Suitable spacers $X^1$ and $X^2$ are each independently derived from one or more amino acids, one or more non-amino acid mono- or diacids (such as acetic acid, priopionic acid, malonic acid, succinic acid, and the like), or non-acid containing spacers (such as alkyl chains, oxyalkyl chains, aminoalkyl chains, and the like), or a combination thereof. For example, preferred spacer moieties are derived from glycine, glycine-glycine, aspartic acid, glycine-aspartic acid, or cysteine-succinic acid. Such spacers may be chosen to vary the distance between the reactive groups as desired. In a preferred embodiment, $X^1$ is derived from glycine-glycine and $X^2$ is derived from aspartic acid. In another preferred embodiment, $X^1$ and $X^2$ are each derived from glycine-aspartic acid.

Figures 1, 1A, 2, 3:
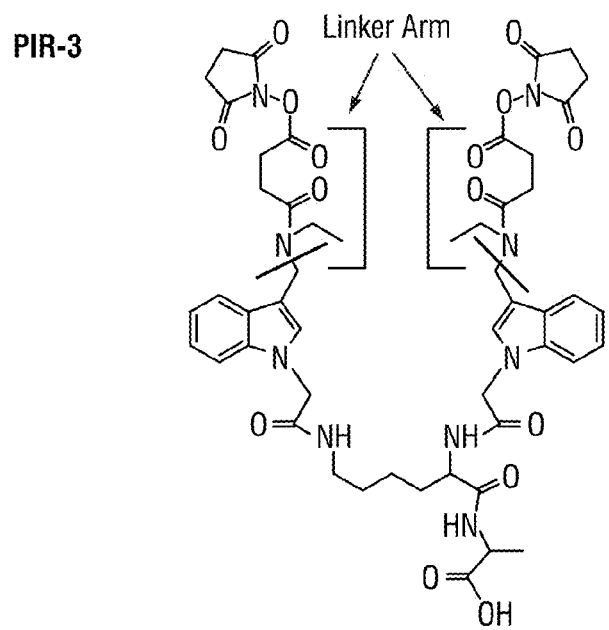
Figure 1B:
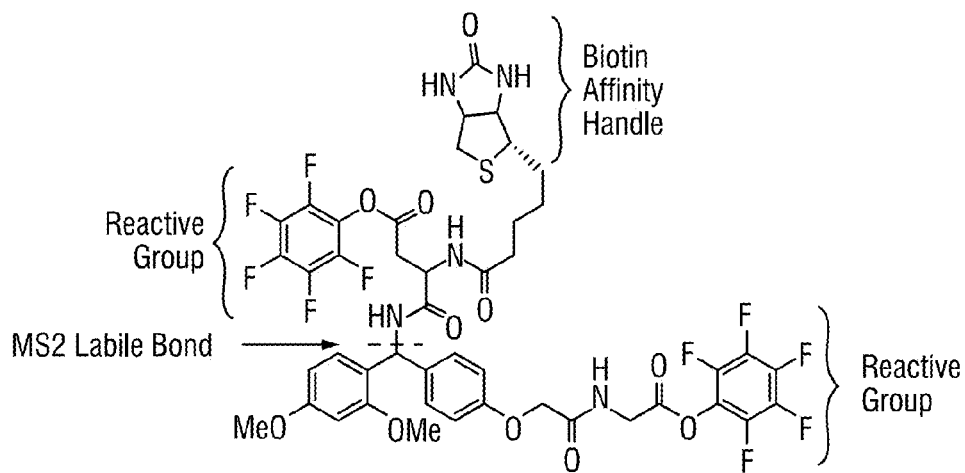
FIGS. 1B, 1C, and 1D show the structures of three embodiments of the crosslinkers of the invention.
Figure 1C:
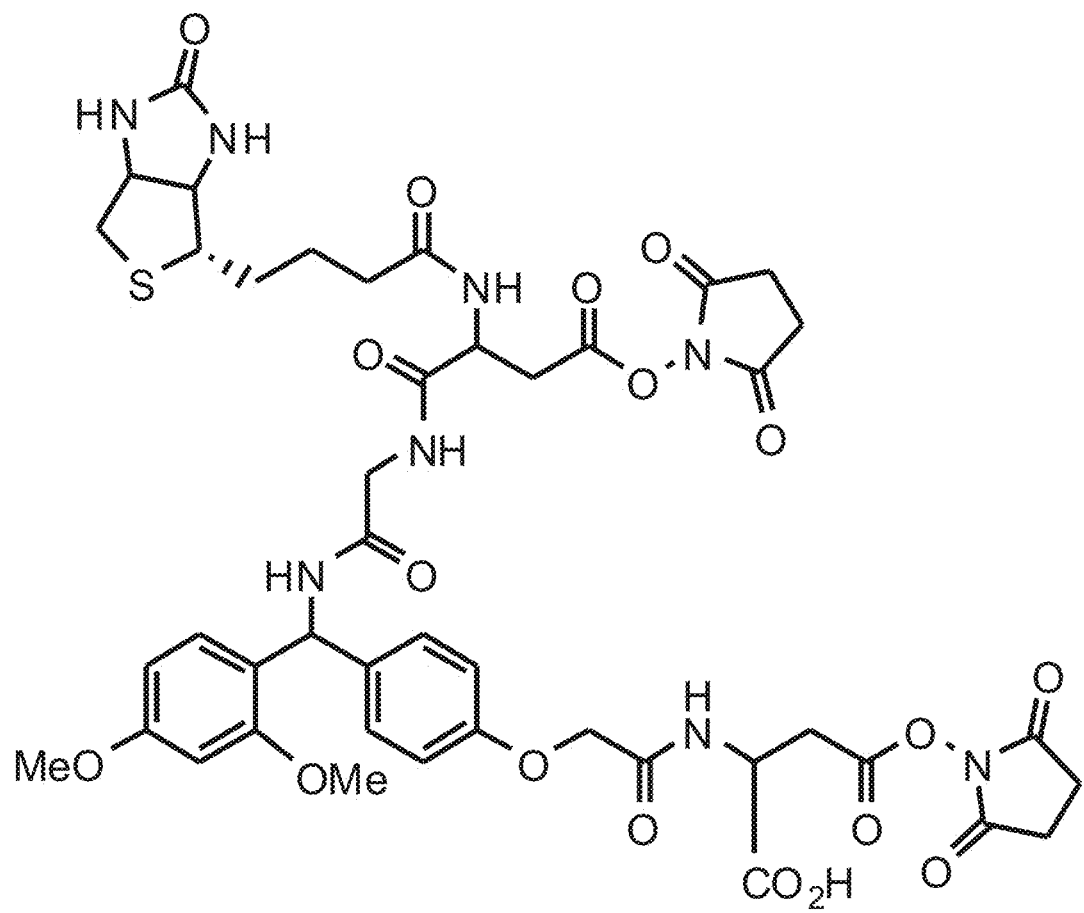
Figure 1D:
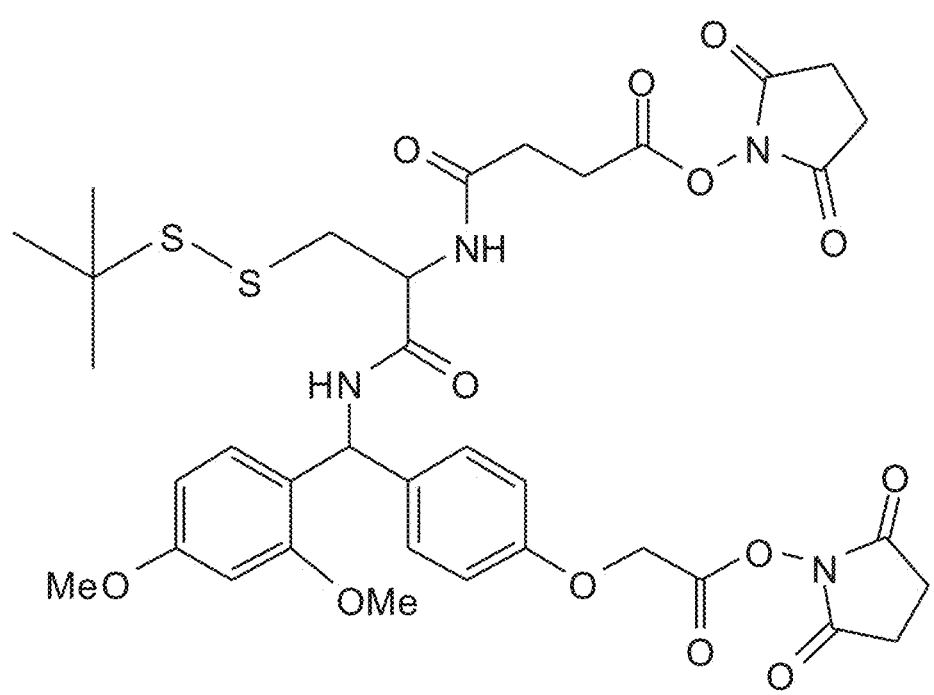

Three specific embodiments of the crosslinkers of the invention are shown in FIGS. 1B, 1C, and 1D.

Any formula given herein is intended to represent compounds having structures depicted by the structural formula as well as certain variations or forms. Thus, any optical isomer, enantiomer, diastereomer, geometric isomer (i.e., cis and trans isomers), tautomer, or atropisomer of the compounds described herein, and any mixture thereof, are considered within the scope of the formula. Additionally, any formula given herein is intended to refer also to any one of hydrates, solvates, and polymorphs of such compounds, and mixtures thereof, even if such forms are not listed explicitly.

MODES OF CARRYING OUT THE INVENTION

The invention offers improved crosslinkers that yield superior results in a method of identifying and characterizing associated proteins and protein chains. All of the inventive crosslinkers obviate the need for a reporter structure by providing only a single low energy MS labile bond, which improves detection efficiency. While some known crosslinkers have only a single MS cleavage site, the crosslinkers of the invention have other advantages as well, such as improved reactivity with the target protein, readily analyzable crosslinked products, and smaller overall size. These additional advantages are discussed below.

The general basis for the method in which the crosslinkers of the invention are employed resides in the ability of the crosslinker chemically to associate specific amino acid residues, preferably lysine residues, which are within the length of separation prescribed by the crosslinker itself. This length of separation may range from about 20 Å to 100 Å, and depends on the specific structures of the spacers and the resulting distance between the functional groups at either end of the crosslinker molecule. In general, shorter distances are desirable; in the crosslinker of Formula (I), the relevant distance is easily controlled by the choice of spacer moieties $X^1$ and $X^2$. For the particular example of the BDRG crosslinker of FIG. 1B, the reacting lysines of the target protein(s) should be about 20 to about 30 Å apart.

In preferred embodiments, the smaller size of the crosslinkers of the invention, as compared, for example, to those of Chowdhury, provides distance constraints for the reacting amino acid (such as lysine) residues that are likely to be more useful for modeling the structure of the protein or protein complex under study. The goal of the method is to identify regions of proteins that are in close proximity to one another in the three-dimensional structure. In general, in order to obtain distance constraints from the crosslinking reaction that will provide useful data for modeling the structure of the protein or protein complex, crosslinkers that have smaller theoretical crosslinking distances are preferred. The theoretical crosslinking distance for the preferred BDRG framework is 27 Å; the theoretical crosslinking distance for the Chowdbury molecule is 43 Å.

The crosslinkers can also be designed so that when cleaved at the MS cleavage site, the two fragments have approximately the same molecular weight, even though the molecules are asymmetric. Equal m/z of the two parts simplifies the interpretation and database search process. Preferably, the values for m/z of the two parts are within about 1 Dalton.

For example, although the BDRG crosslinker of FIG. 1B is an asymmetric crosslinker, it is designed such that the two crosslinker portions on either side of the cleavable bond have approximately the same molecular weight. For example, after cleavage, the two crosslinker portions BD and RG give similar masses of 339 and 340, respectively, even though their compositions are very different. Similar masses of the released crosslinker portions make it easier to identify the modified peptides by running a database search that takes into account a single mass modification on lysine of 339.5 with a three (3) Dalton window. An alternative crosslinker, shown with NHS reactive groups of FIG. 1C, also has this property. Preferably, the two crosslinker portions exhibit m/z values within about 1 Dalton of each other.

Figure 2A:
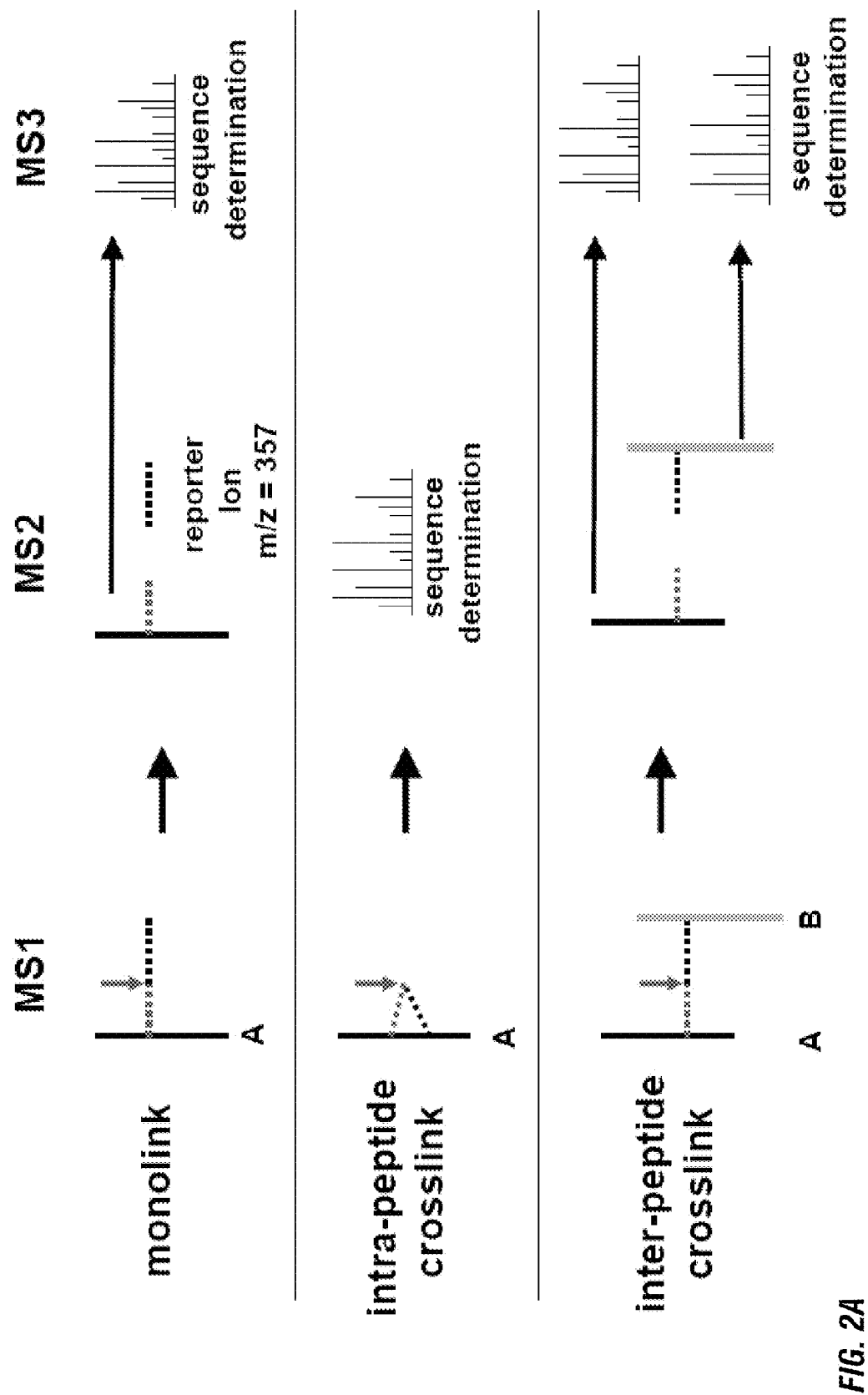
Figure 2B:
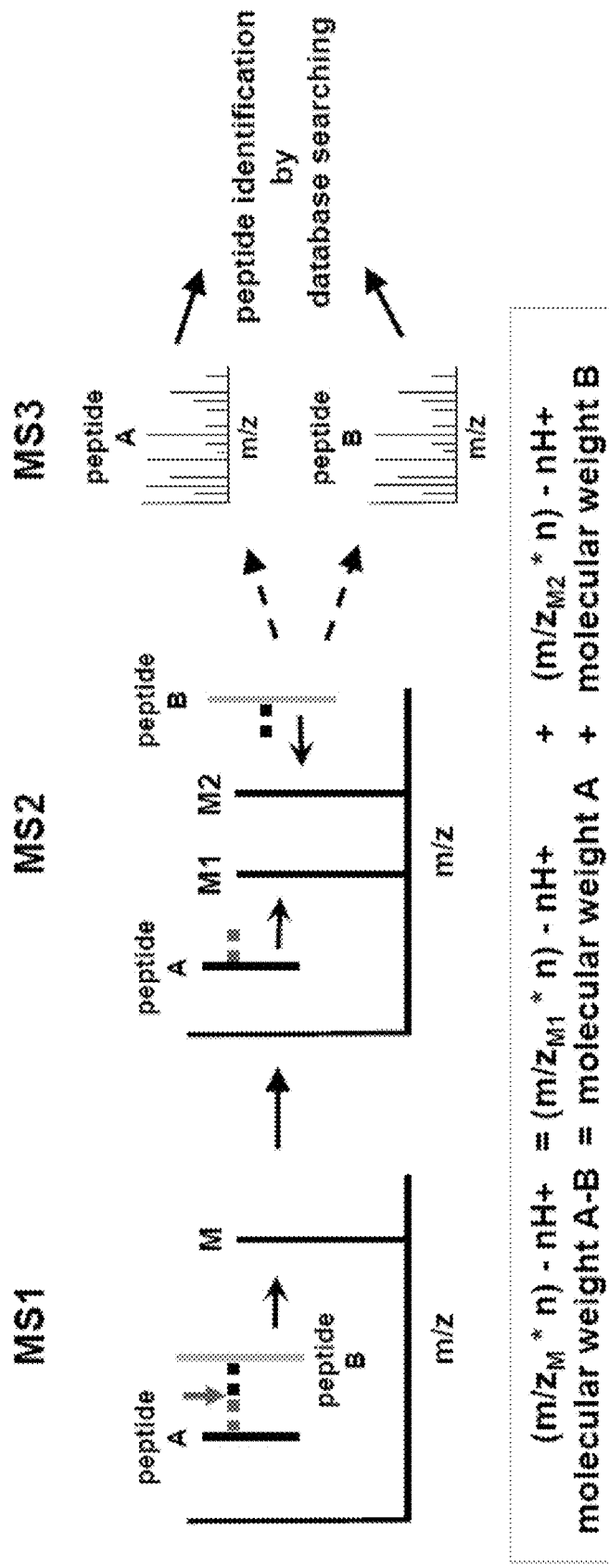
Figure 3:
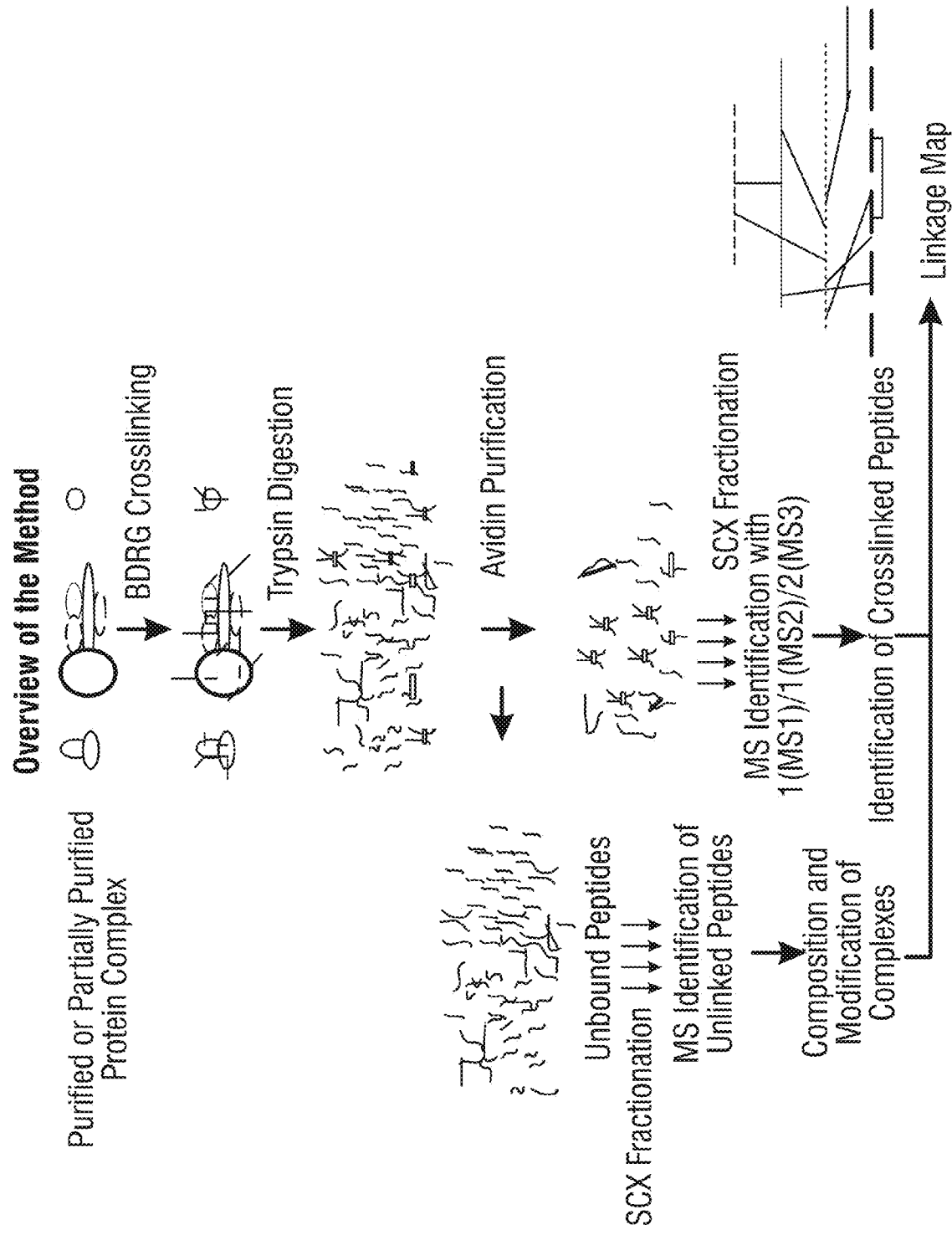

The general procedure for the inventive method is illustrated in FIGS. 2A-2B and 3. The following exemplary procedure, described for amino reactive groups, may be modified by one of skill in the art for other amino acid-reactive moieties.

1. A sample, which may be a purified protein, a partially purified protein complex, a cellular extract, or a biological fluid or any other formulation that contains proteins, is treated with the crosslinking agent. By way of example, in the case of a crosslinker comprising a BDRG framework, the reactive groups are displaced by ε-amino groups of lysine residues and free amino termini, leaving the remainder of the crosslinker covalently coupled to the free ε-amino group of the lysine residue or free amino termini through a peptide linkage. In the case of monolinks, one reactive group reacts with a peptide amino group, and the other is hydrolyzed to a carboxylic acid.

2. The resulting reaction mixture is treated with a proteolytic enzyme, such as trypsin, endoprotease LysC, or GluC, and preferably trypsin, to strip away much of the amino acid sequence around the residue(s) which are coupled to the crosslinker, thus reducing the size of the crosslinker-modified peptides to those that are amenable to liquid chromatography-mass spectrometry (LC-MS) analysis for peptide identification. Trypsin cleaves immediately downstream of either an arginine or lysine residue. In FIG. 5, which depicts the β-lactoglobulin case, several of the peptides are depicted with an alanine residue preceding the cleavage site (represented by a dot). It is known that alanine is upstream of the detected peptide because the sequence of the protein (once it has been identified) is known and the detected peptide has an upstream alanine residue. The two most likely reasons for finding an upstream residue other than R or K are 1) the protein has been cleaved by a trypsin-independent mechanism, or 2) in vivo processing of the protein results in multiple N-terminal ends.

3. The components of the mixture of peptides that contain the crosslinker and the crosslinker-modified peptides are purified by affinity chromatography using the affinity ligand, which, in the case of BDRG, is biotin with avidin used as the binding partner.

4. Having obtained the components of the mixture which retain the crosslinker, the mixture is subjected to LC-MS.
   a. The first mass spectrum obtained, MS1, shows results where the crosslinker is still present, and the MS labile bond has not been cleaved.
   b. In a second step, the parent ion from the MS1 event is isolated and subjected to CID to fragment the ion by cleavage at the cleavage site. Thus, for this second mass spectrum, MS2, the sample has been subjected to a low energy cleavage step using standard collision energy settings for fragmentation of peptides using, for example, the LTQ-Orbitrap™ mass spec from Thermo Scientific, which is 35% collision energy. This results in preferential breakage of the low energy MS labile bond of the cleavage site moiety. A gross mass spectrum is obtained showing the mass/charge (m/z) of each component peptide/linker remnant. As shown in FIG. 2A, when a monolink is present, the remainder of the linker shows up in the spectrum as a useful diagnostic ion; intrapeptide and interpeptide links are distinguished by m/z differences between MS1 and MS2. Also, however, as shown in FIG. 2A, when the linkage is an intrapeptide (loop) linkage, there is sufficient energy to effect fragmentation equivalent to that obtained in the MS3 stage discussed below in the case of monolinks and interpeptide linkages.

c. In third and fourth steps, each of the component peptide/linker remnant ions derived from a monolinks or an interpeptide link is individually isolated and subjected to CID to produce an MS3 spectrum. During these steps the peptide/linker fragments primarily along the peptide backbone producing a series of fragment ions. This MS3 spectrum provides the information that is used by database search algorithms to identify the sequence of the peptide associated with the remainder of the linker.

As noted, looplinked peptides will be found in searches of the MS2 spectrum. The first CID event results in fragmentation of the crosslinker MS cleavable bond as well as fragmentation along the peptide backbone.

Thus, as shown in FIG. 2A, monolinks, crosslinks and looplinks can be distinguished at the MS2 level by virtue of the presence of the diagnostic ion representing the residue of a linker in the case of a monolink, the presence of two ions retaining portions of the linking moiety that have a combined mass (after taking into account their charge states) equal to that of the parent ion in the case of the crosslink, and a fragmentation spectrum of the peptide in the case of a looplink.

In a final analytical step, the sequenced peptides—i.e., those peptides whose sequence is evidenced from the detailed mass spectrum after sequence database searching, serve to identify the protein, the location of the protein at which the modification occurred, and the like. The sequence of one or more of the peptides may also be determined directly from MS3 by comparison to spectral databases.

The overall process is shown in more detail for interpeptide links in FIG. 2B. A single peak in MS1 becomes two major peaks in MS2, each of which is subjected to LC-MS with additional fragmentation in MS3 to determine structure.

An alternative outline of the overall procedure is shown in FIG. 3, with biotin affinity ligand as an example. After crosslinking, the protein sample is subjected to trypsin digestion resulting in multiple fragments, some of which are linked. The crosslinker-modified peptides are separated and purified by association with avidin. The resulting peptides are separated by strong cation exchange fractionation (SCX fractionation) followed by the LC-MS steps MS1, MS2, and MS3 and sequence analysis outlined above. The unbound peptides can also be fractionated, separated and identified (sequenced) by mass spectroscopy, analogous to MS3 above.

Figure 8:
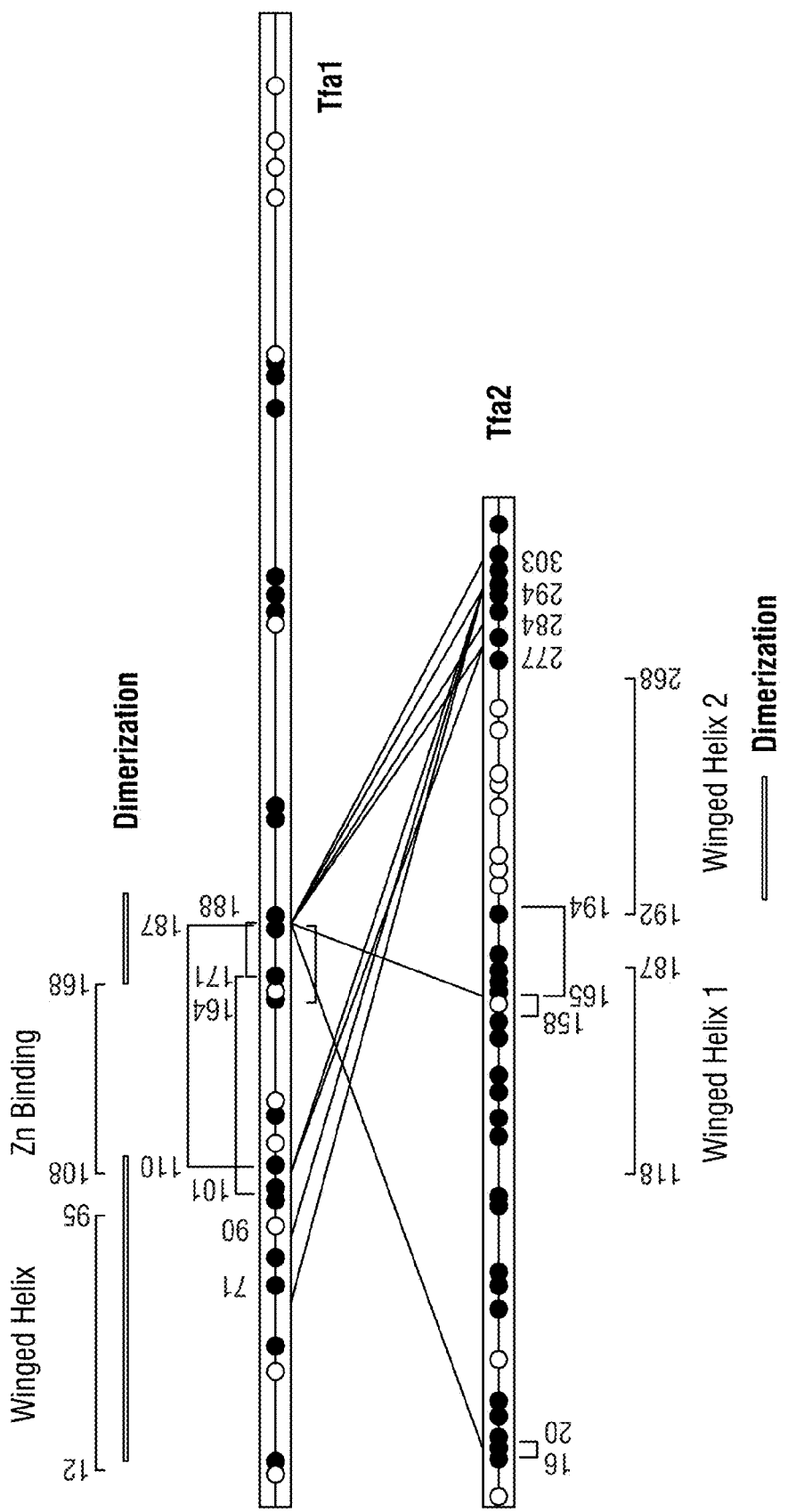
FIG. 8 shows a map of the crosslinked peptides of the heterodimeric complex TFIIE.

The resulting sequences, combined with knowledge of the sequences of the proteins in the complex (obtained from standard databases) permit construction of a linkage map similar to that shown for TFIIE in FIG. 8.

Crosslinkers of the invention are prepared according to general Scheme 1. Those skilled in the art will recognize other methods of standard resin-based or solution-based chemistry are applicable. One skilled in the art will also be able to choose appropriate protecting groups for the synthesis.

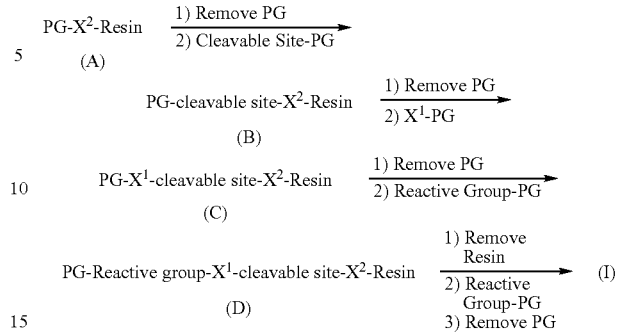

Scheme 1.

As depicted in Scheme 1, a suitable synthesis resin may be purchased with spacer $X^2$ in place (optionally protected with a protecting group, PG) or the optionally protected $X^2$ spacer may be appended to the resin using known peptide coupling methods (formula (A)). Removal of the $X^2$ protecting group, if necessary, is followed by reaction with an optionally PG-protected moiety comprising the low energy MS cleavable site to generate a compound of formula (B). Removal of the protecting group, if necessary, and coupling with an optionally protected $X^1$ spacer yields a compound of formula (C). Removal of the $X^1$ protecting group, if necessary, and reaction with a suitably protected reactive group provides a compound of formula (D). The molecule is cleaved from the resin, reacted with an optionally protected reactive group, and optionally deprotected, to yield crosslinkers of Formula (I).

The following Examples are offered to illustrate, but not to limit, the invention.

Example 1

Synthesis of a Crosslinker with a BDRGD Framework and NHS Reactive Groups

1. Swell Fmoc-Glycine-HMPB-BHA resin (NovaBiochem) by addition of N,N-dimethylormamide (DMF) for 30 min.
2. Wash resin 3×5 mL with DMF.
3. Deprotect Fmoc using 2×5 mL 20% piperidine in DMF with $N_2$ agitation for 10 min each treatment. Wash the resin with 5×2 mL DMF.
4. Add Fmoc-RINK linker (2 eq, NovaBiochem) using benzotriazol-1-yl-oxytripyrrolidinophosphonium hexafluorophosphate (PyBOP, 3 eq), N-hydroxybenzotriazole (HOBt, 3 eq) and N,N-diisopropylethylamine (DIPEA, 6 eq) in DMF with $N_2$ agitation for 2 hours.
5. Repeat steps 2 to 4 with Fmoc-Aspartic acid-(2-phenylisopropylester)-OH (NovaBiochem).
6. Repeat steps 2 and 3. Then add pre-activated Biotin-ONp (NovaBiochem) in DMF with $N_2$ agitation for 2 hours (ONp =O-nitrophenyl).
7. Wash 3×5 mL with DMF, then 3×5 mL with dichloromethane (DCM).
8. Cleave the final product from the resin by addition of 2 mL 1% trifluoroacetic acid (TFA) in dichloromethane for 2 min, followed by washing with 1 mL methanol. Repeat the cleavage and wash steps 10 times. Pool the eluates. This step also removes the 2-phenylisopropylester protection group.
9. Dry the eluate under reduced pressure.
10. Activate the carboxyl group of glycine and the β-carboxyl group of aspartic acid by addition of N,N'-diisopropylcarbodiimide (DIC) (6 eq) and NHS (6 eq) at a concentration of 50 mM in dry DMF overnight.

These steps were performed to obtain the BDRGD/NHS crosslinker shown in FIG. 1C.

Example 2

Synthesis of the BDRG Crosslinker

The BDRG crosslinker was synthesized by Almac Sciences (England) by the method in Example 1, substituting a glycine-glycine spacer for the glycine-aspartic acid spacer, and pentafluorophenol for NHS.

The free acid of the disulfide protected crosslinker was synthesized using 2-chlorotrityl resin. First, the Fmoc-RINK linker (2 eq, NovaBiochem) was loaded onto 2-chlorotrityl resin in DIPEA (6 eq) in DMF. Fmoc-Cys(tButhio)-OH (NovaBiochem) was added according to standard Fmoc solid phase peptide synthesis procedures. Finally, succinic anhydride was added in DIPEA (6 eq) in DMF. The free acid was cleaved from the resin using 1% TFA and dried under reduced pressure. The free acid was then activated by addition of DIC (6 eq) and NHS (6 eq) at a concentration of 50 mM in dry DMF overnight.

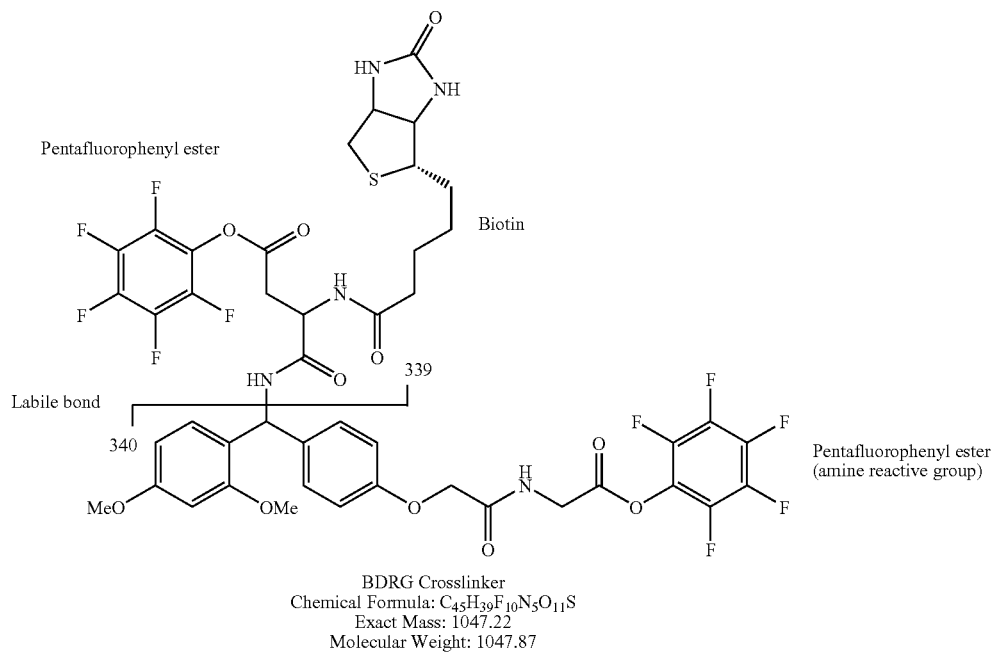 [SMILES: COc1ccc(C(NC(=O)C(CC(=O)Oc2c(F)c(F)c(F)c(F)c2F)NC(=O)CCCC[C@@H]2SCC3NC(=O)NC32)c2ccc(OCC(=O)NCC(=O)Oc3c(F)c(F)c(F)c(F)c3F)cc2)c(OC)c1]

BDRG Crosslinker
Chemical Formula: $C_{45}H_{39}F_{10}N_5O_{11}S$
Exact Mass: 1047.22
Molecular Weight: 1047.87

Example 3

Preparation of a Crosslinker with a GRCSS Framework and NHS Reactive Groups

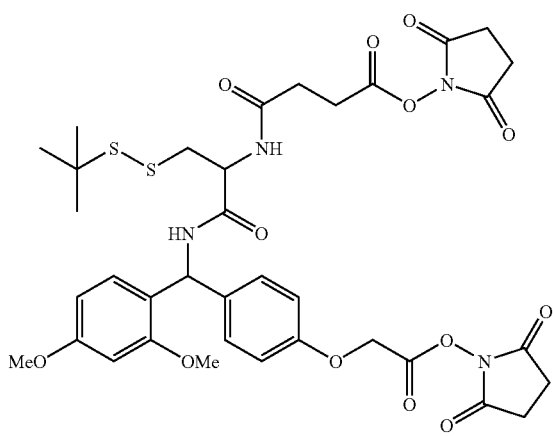 [SMILES: COc1ccc(C(NC(=O)C(CSSC(C)(C)C)NC(=O)CCC(=O)ON2C(=O)CCC2=O)c2ccc(OCC(=O)ON3C(=O)CCC3=O)cc2)c(OC)c1]

Example 4

Crosslinking of the Monomeric Protein, β-Lactoglobulin

β-Lactoglobulin (50-100 μg) was dissolved in 100 mM HEPES (pH 8.0; 100 μL) buffer. The BDRG crosslinker (2 μL; 2 mM in DMF) was added to the protein solution. After 60 minutes at room temperature, the reaction was quenched by addition of 1 M ammonium bicarbonate (10 μL). The crosslinked sample was precipitated with acetone to remove unreacted BDRG and resuspended in 8 M urea in 50 mM Tris pH 8.0. After diluting the urea concentration to 1.3 M the sample was digested by treatment with 5-10 μg trypsin at 37° C., overnight. The resultant crosslinker-modified peptides were purified by C18 chromatography column and dried under reduced pressure. The peptides were resuspended in 1× phosphate buffered saline and enriched by avidin affinity chromatography. The resulting mixture was separated into 5 fractions by strong cation exchange chromatography to further reduce sample complexity. Each fraction was analyzed using a high mass accuracy LTQ-Orbitrap using the following method: one MS1 event followed by one MS2 event based on the most abundant ion in the previous MS1 spectrum, and then two MS3 events were based on the two most abundant ions in the MS2 event.

Figure 4A:
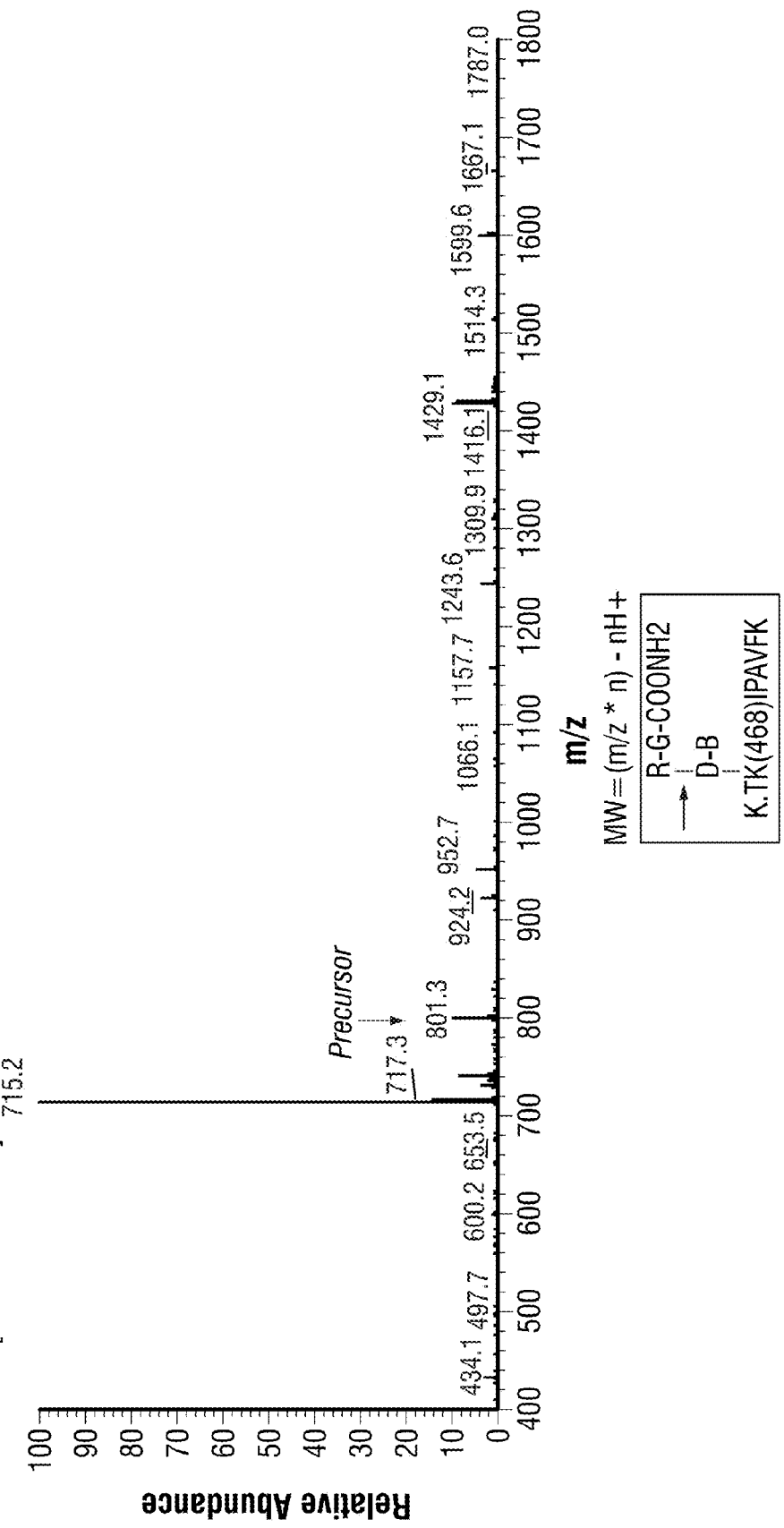
FIG. 4A-C shows the results of MS1, MS2 and MS3 for a monolinked peptide (SEQ ID NO:1). The number shown in parentheses in the sequence indicates the molecular weight of the lysine residue modified by the mass of the biotin-aspartic acid ("BD") moiety derived from the BDRG crosslinker. The lysine (K.) in the peptide sequences precedes the residue following the lysine in the protein sequence from which the peptide was derived.
Figure 4B:
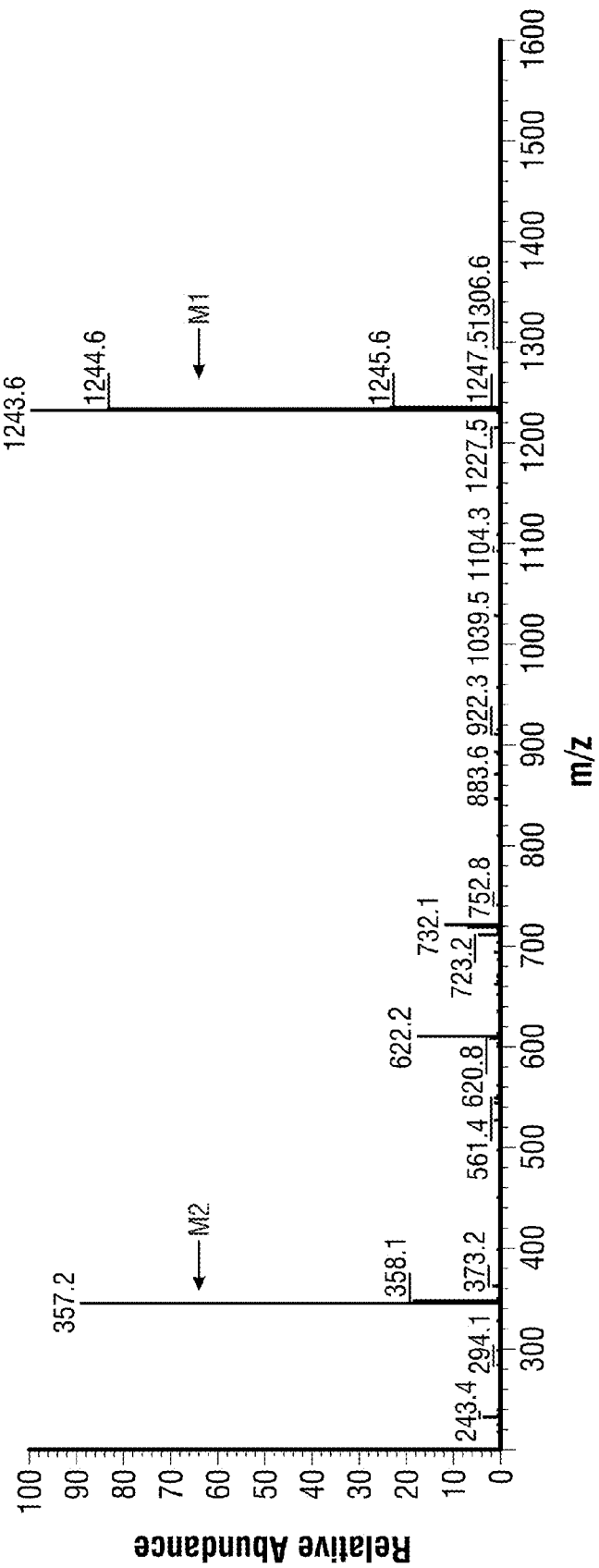
Figure 4C:
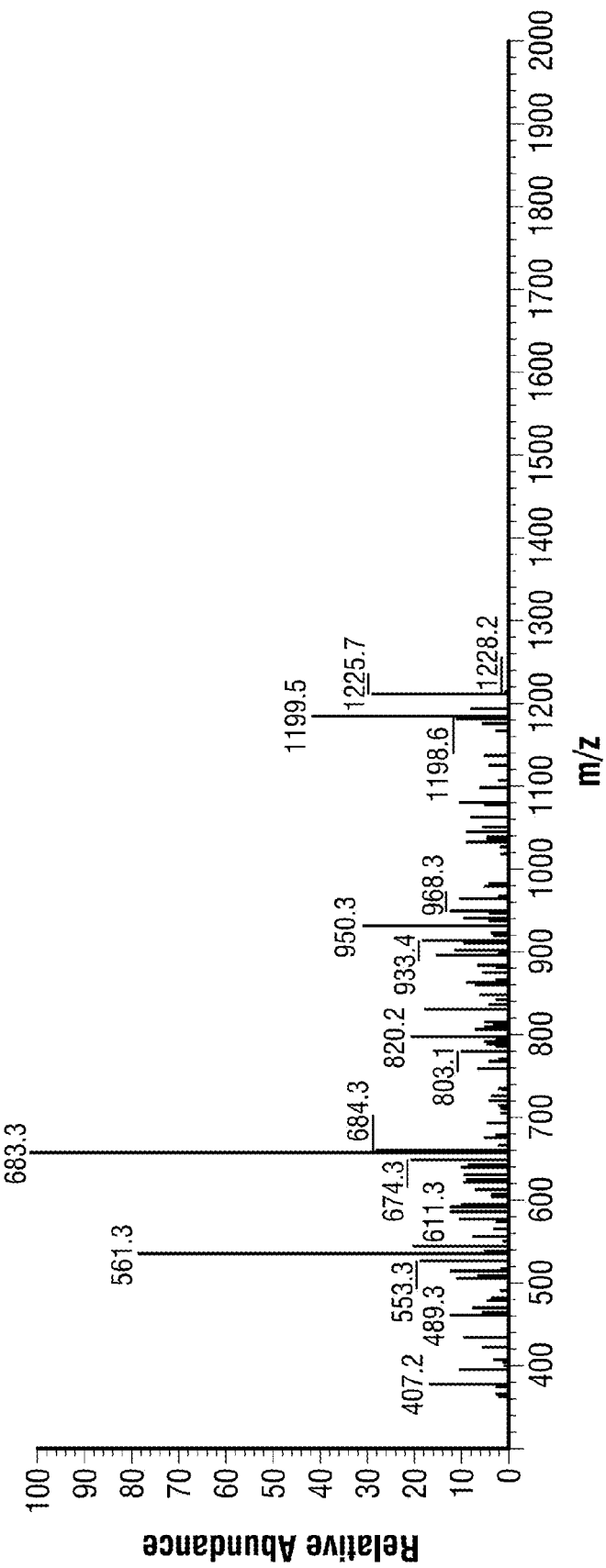

The mass spectra generated in MS1, MS2 and MS3 of the BDRG modified peptide derived from bovine β-lactoglobulin illustrate the detection of a monolink. As shown in FIG. 4, MS1 provided the spectrum prior to cleavage of the linkage contained in BDRG where B refers to biotin, D refers to aspartic acid residue, R refers to the RINK linkage, and G refers to glycine. The ion with a m/z of 801.3 was selected by the mass spectrometer for MS2 analysis. During this analysis, the low energy MS cleavable bond was broken generating the diagnostic ion of 357 m/z. The remainder of the parent molecule, including the BD residue, was observed at m/z 1243.6. These two ions were observed as the most intense ions. MS3 shows the spectrum resulting from fragmentation of the ion with m/z 1243.6, which permitted identification of the sequence of the relevant protein using the SEQUEST™ algorithm (Eng, J. K., et al., *J. Am. Soc. Mass Spectrom.* (1994) 5:976-989), which is incorporated herein by reference.

Figure 6:
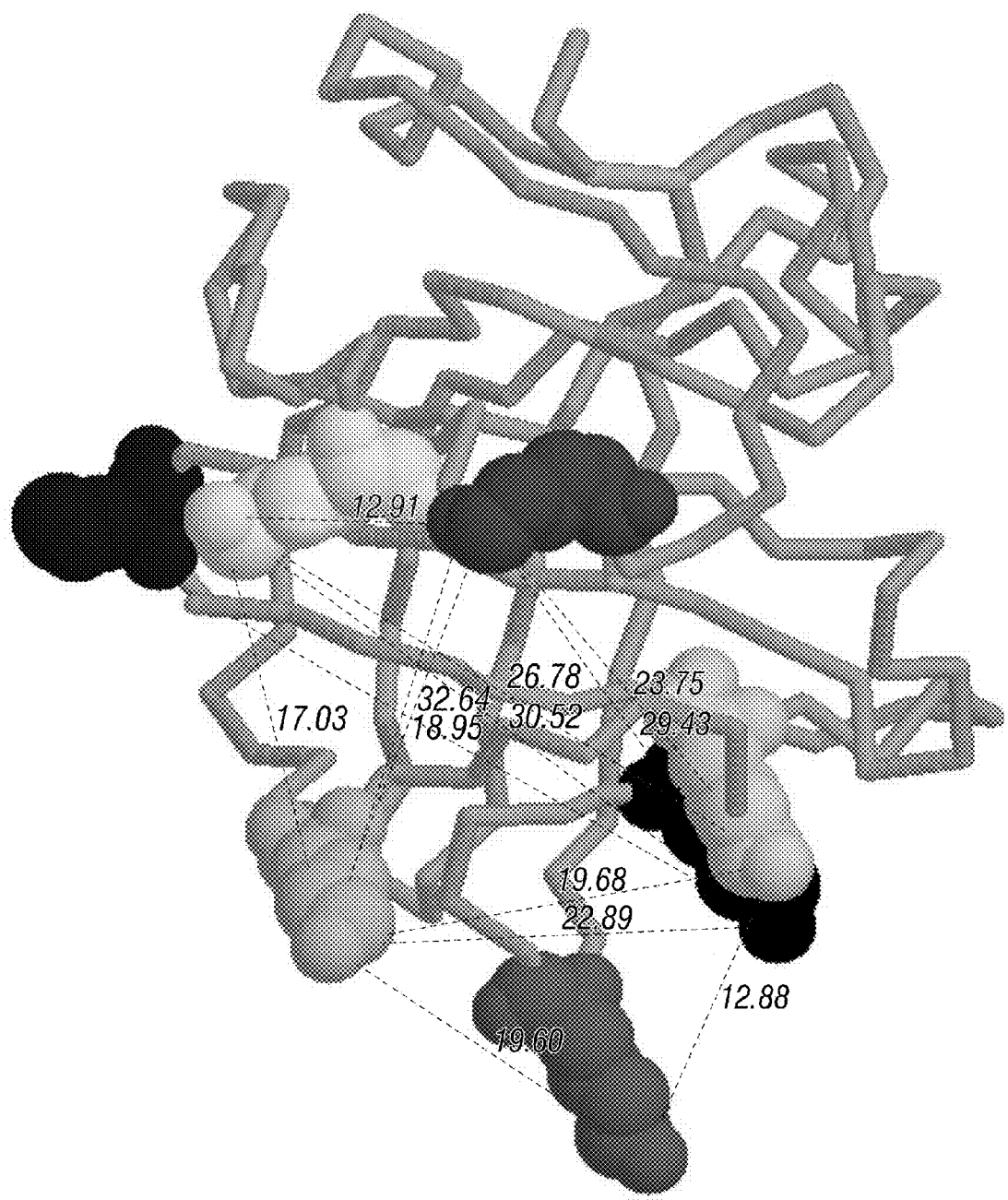
FIG. 6 shows a three-dimensional construct of β-lactoglobulin with the positions and distances of the crosslinked residues indicated.
Figure 7A:
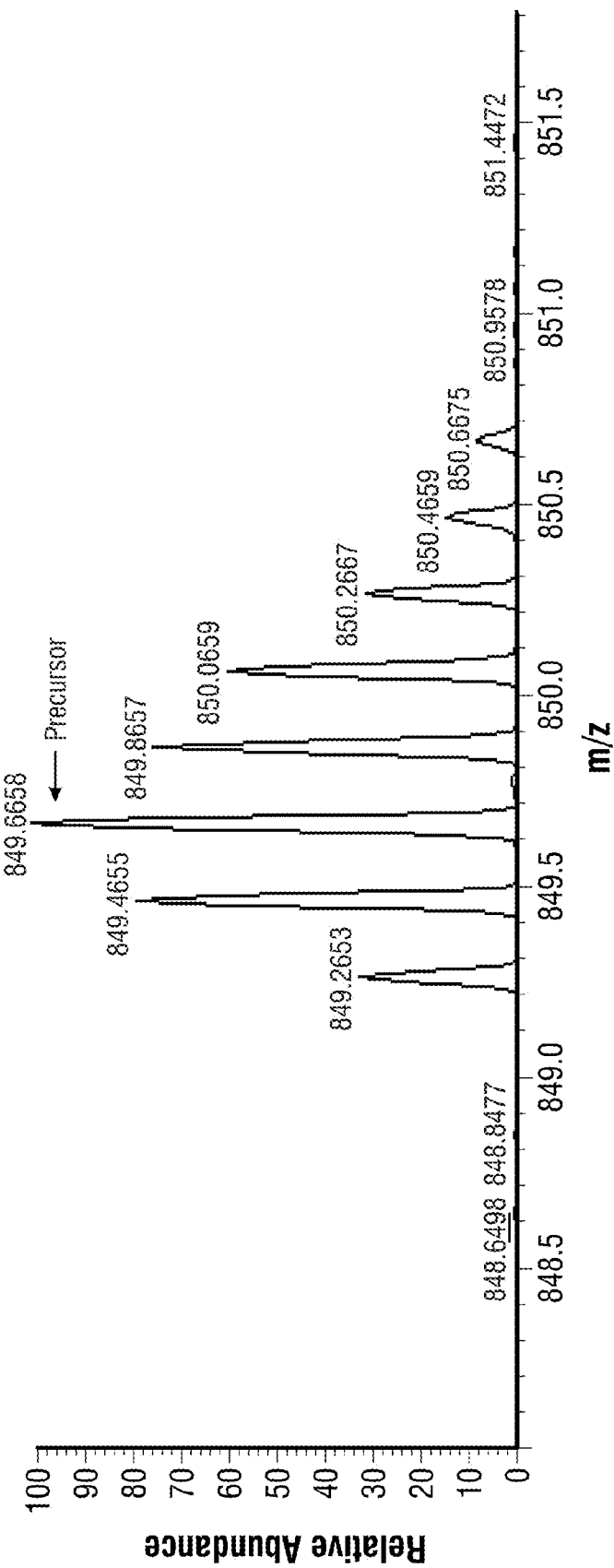
FIG. 7A-D shows the results of MS1, MS2 and MS3 derived from a crosslinked peptide (SEQ ID NOS:10-11) from the heterodimeric complex Transcription Factor II E ("TFIIE"). As in FIG. 4, the number shown in brackets in the sequence indicates the molecular weight of the lysine residue modified by the mass of the moiety derived from the BDRG crosslinker. The lysine (K.) or arginine (R.) in the peptide sequences precedes the residue following the lysine or arginine in the protein sequence from which the peptide was derived.
Figure 7B:
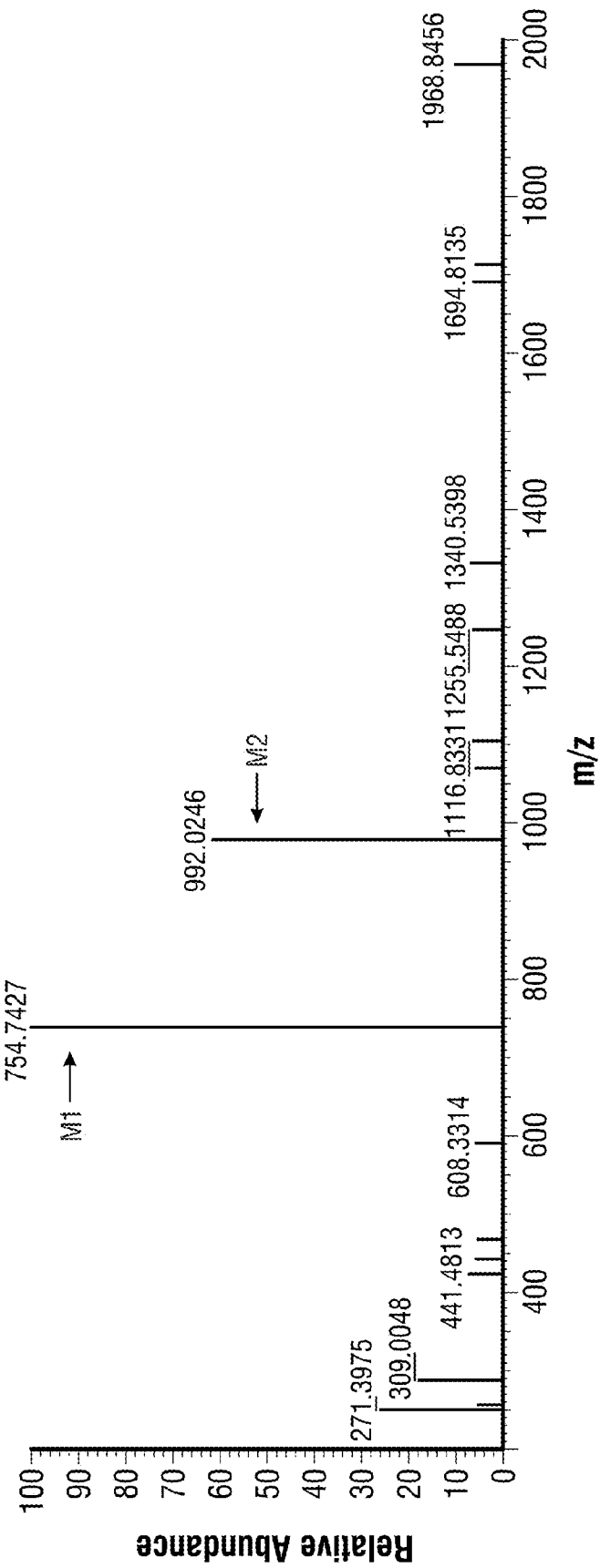
Figure 7C:
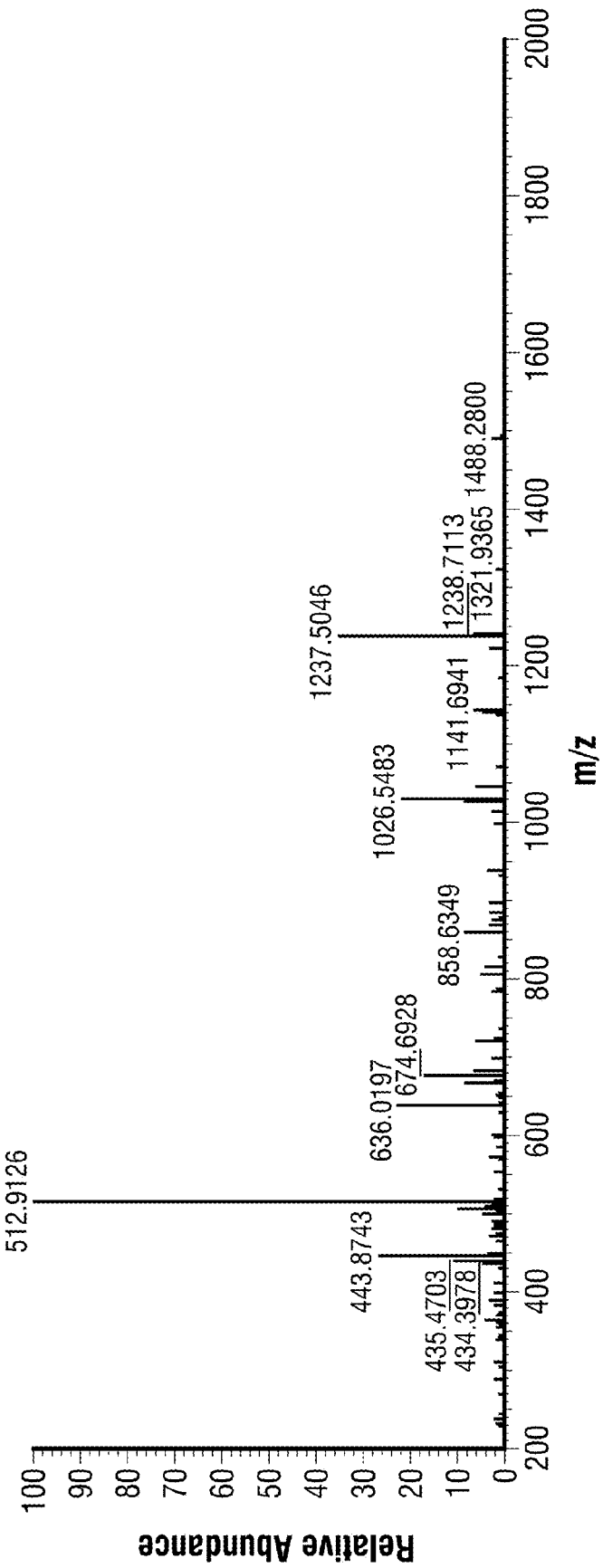
Figure 7D:
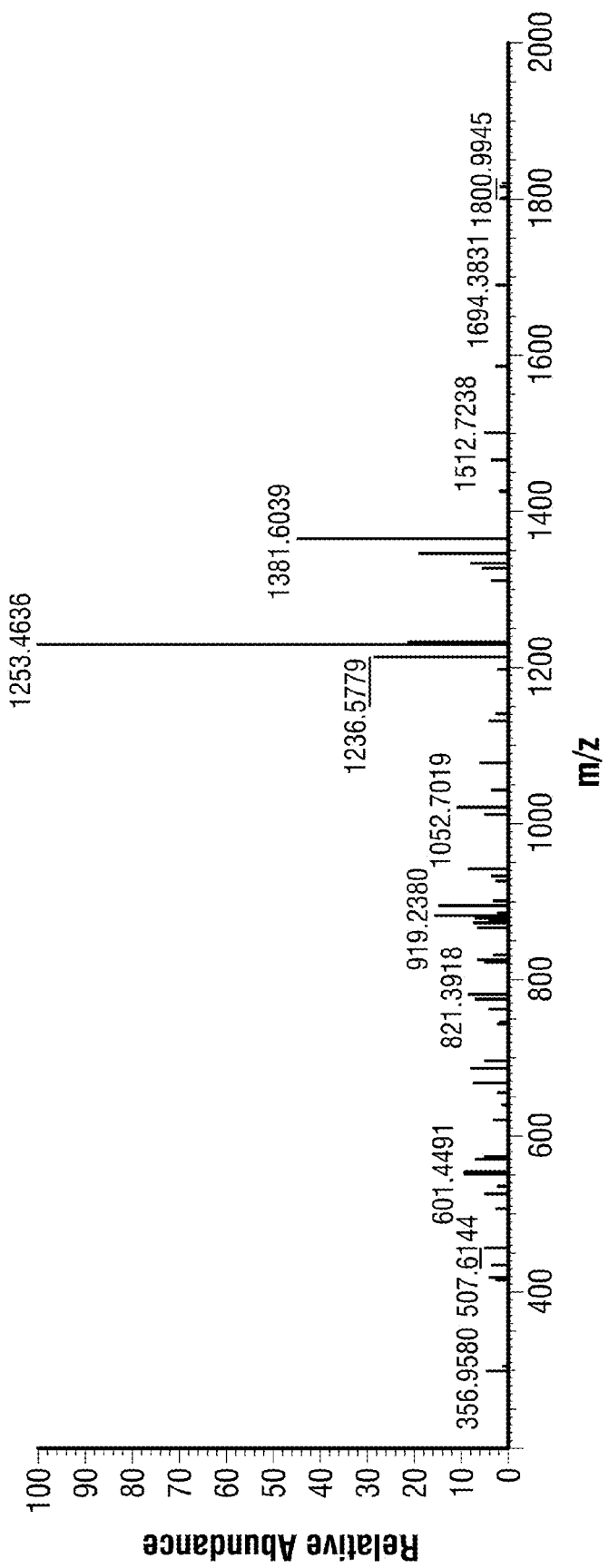

The various peptides obtained in crosslinker-modified molecules are shown in FIG. 5. As noted above, although trypsin commonly cleaves immediately downstream of arginine (R) or lysine (K), cleavage appears to have occurred immediately downstream of alanine (A), in some cases. FIG. 6 shows the position of some of these peptides on the X-ray crystal structure of the protein. Importantly, the crosslinker-modified residues are separated by 5.6-30.5 Å, (average 15.8 Å) demonstrating the utility of the method of the invention to identify resides which are in close proximity to one another.

Example 5

The Heterodimeric Complex TFIIE from the Yeast *Saccharomyces cerevisiae*

The TFIIE protein is composed of two polypeptide subunits TFA1 and TFA2. Purified TFIIE (50 µg) was dissolved in 100 mM HEPES (pH 8.0) buffer (10 µL). The BDRG crosslinker (2 µL; 25 mM in DMF) was added to the protein solution. After 60 minutes at room temperature, the reaction was quenched by addition of 1 M ammonium bicarbonate (10 µL). The crosslinked sample was precipitated with acetone to remove unreacted BDRG and resuspended in 8 M urea in 50 mM Tris pH 8.0. After diluting the urea concentration to 1.3 M the sample was digested by treatment with 5-10 ug trypsin at 37° C., overnight. The resultant crosslinker-modified peptides were purified by C18 chromatography column and dried under reduced pressure. The peptides were resuspended in 1×PBS and enriched by avidin affinity chromatography, and then separated into 5 fractions by strong cation exchange chromatography to further reduce sample complexity. Each fraction was analyzed using a high mass accuracy LTQ-Orbitrap using the following method: one MS1 event followed by one MS2 event based on the most abundant ion in the previous MS1 spectrum, and then two MS3 events based on the two most abundant ions in the MS2 event.

As shown in FIG. 7, in MS1, a significant peak at 4243.35 was detected which generated, upon cleavage of the low energy MS labile bond, significant peaks representing the two portions of the crosslinked peptides whose masses added up to the mass of the original crosslinked molecule, as shown for MS2. MS3 spectra of the two daughter ions were obtained which were used to identify the peptide sequence using SEQUEST™ (Eng, J. K., et al., supra).

FIG. 8 shows an analysis of several results obtained for TFIIE in this manner. Black dots indicate lysine residues identified with a BDRG modification. White dots represent lysines residues which were not identified with a BDRG modification. Lines indicate lysine residues which were identified as being crosslinked by BDRG. The numbers indicate the amino acid position in the sequence of the indicated proteins. Previously identified structural and functional regions are listed below each protein.

Example 6

Crosslinking of Yeast RNA Polymerase II

Figure 9:
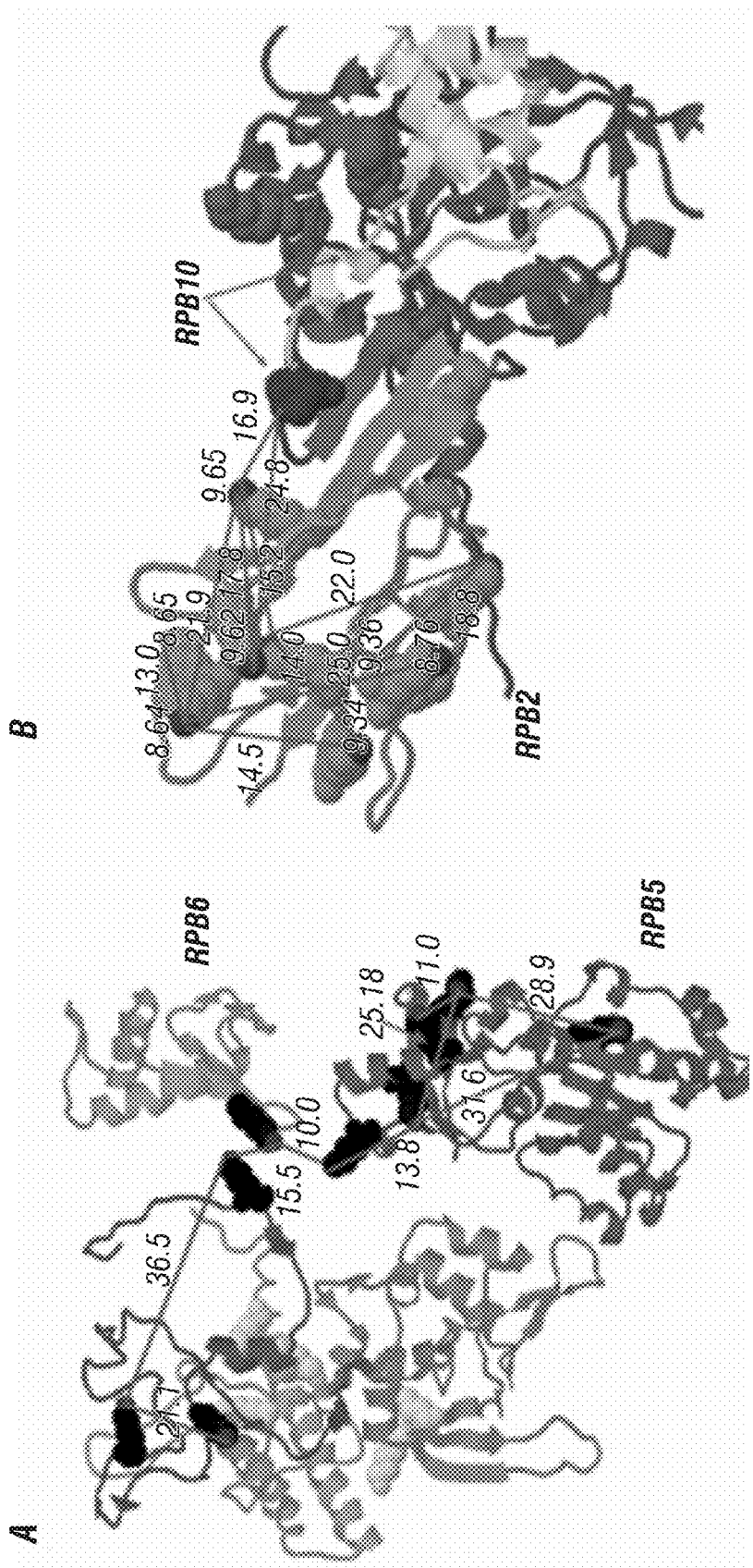
FIG. 9 shows a map of a subset of BDRG crosslinks onto the structure of Pol II. Grey lines connect crosslinked lysine residues. The calculated distances (in angstroms) between crosslinked residues are indicated. Panel A. Identified crosslinks involving RPB1, RPB5 and RPB6. The RPB1 regions are the clamp core 1 (residues 1-95), clamp head (96-234), and clamp core 2 (235-346). Panel B. Identified crosslinks involving RPB2 and RPB10. The RPB2 regions are the hybrid binding region 1 (750-852), the wall region (853-973), and the hybrid binding region 2 (974-1127). Notably, the crystal structure lacks the tail sequence of RPB10, NPLEKRD (SEQ ID NO:12), ending at the proline (spacefilled region indicated by an arrow). The crosslinking method permits positioning of this region.

Pol II was purified from a strain carrying a tandem tagged 3×FLAG-6×His RPB3 subunit by anti-FLAG affinity chromatography followed by Ni$^{2+}$ affinity chromatography. The complex was ~90% pure as estimated by Coomassie stained SDS-PAGE analysis and mass spectrometry analysis. The usual yield of Pol II is 100 pmols from 2 liters of cells. The Pol II preparation was subjected to the BDRG crosslinking approach using the BDRG crosslinker as described in the preceding examples. Five inter-protein cros links, 15 intra-protein cros links, 15 looplinks, and 117 monolinks were identified. Upon mapping the location of the crosslinked resides onto the structure of Pol II, it was clear the cros slinks identified residues which are in close proximity to one another (FIG. 9). The maximum distance between crosslinked residues was 19.91 Å. These results revealed the method identified crosslinks within a large macromolecular complex, and the observed crosslinks provided information useful for mapping subunit architecture.

The invention claimed is:

1. A crosslinker compound useful for modifying proteins for mass spectral analysis which compound is of Formula (I):

$$\text{Reactive group} - X^1 - \text{cleavable site} - X^2 - \text{Reactive group;}$$

(I)

wherein each of $X^1$ and $X^2$ is independently a branched or linear spacer moiety comprising a chain of 2-10 atom members selected from the group consisting of carbon, nitrogen, sulfur, and oxygen, wherein each carbon atom is optionally substituted with =O; wherein at least one of $X^1$ and $X^2$ is substituted by an "affinity ligand" that is selected from group consisting of biotin, desthiobiotin, a perfluorocarbon alkyl chain, tert-butyl disulfide, and S-acetyl thioacetate;

wherein each "reactive group" is independently a leaving group that reacts with an amine, hydroxyl, sulfhydryl, or carboxyl group of a protein to form a covalent bond with the protein;

wherein the cross-linker compound of Formula (I) contains a single MS labile bond that is located at the cleavable site, wherein the cleavable site is (a) a moiety of formula (1), wherein R is H or alkyl $C_{1-6}$:

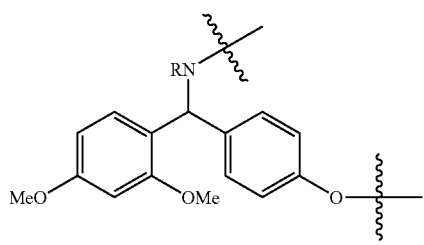

(b) a moiety of formula (2), wherein R is H or alkyl $C_{1-6}$:

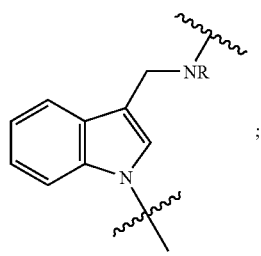

or (c) a moiety of formula (3):

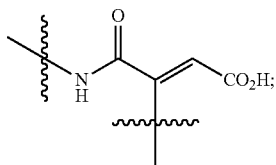

wherein the wavy line in each of the (a)-(c) cleavage site moieties indicates linkages to the spacer moieties $X^1$ and $X^2$; and wherein the crosslinker portions on either side of the MS labile bond have approximately the same molecular weight, such that the m/z (mass/charge number) value for each is within about 1 Dalton of the other.

2. The compound of claim 1, wherein the reactive groups are independently selected from the group consisting of: pentafluorophenol and structural variants thereof, N-hydroxysuccinimide and structural variants thereof, aryl azides, carbodiimides, hydrazides, hydroxymethylphosphines, imidoesters, isocyanates, maleimides, vinyl sulfones, and pyridyl disulfides.

3. The compound of claim 1, wherein the reactive groups are independently pentafluorophenol, N-hydroxysuccinimide, N-hydroxysulfosuccinimide, or 4-sulfotetrafluorophenol.

4. The compound of claim 1, wherein the reactive groups are independently selected from the group consisting of pentafluorophenol and N-hydroxysuccinimide.

5. The compound of claim 1, wherein the reactive groups are $R^1$—O—, wherein each $R^1$ is independently pentafluorophenyl, N-succinimidyl, N-sulfosuccinimidyl, or 4-sulfotetrafluorophenyl, and wherein each $R^1$—O— group is connected to a carbonyl group of $X^1$ or $X^2$ to form an ester, and is displaceable by the nitrogen of protein amino group.

6. The compound of claim 5, wherein each $R^1$ is independently pentafluorophenyl or N-succinimidyl.

7. The compound of claim 1, wherein the cleavage site is a moiety of formula (1):

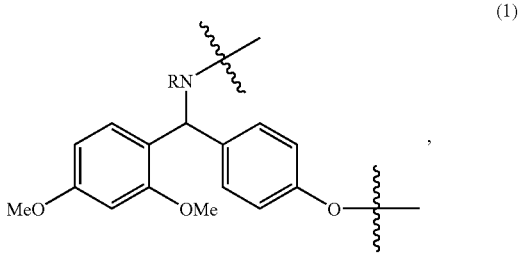

wherein R is H or alkyl $C_{1-6}$.

8. The compound of claim 1, wherein the affinity ligand is biotin.

9. The compound of claim 1, wherein $X^1$ and $X^2$ are each independently derived from one or more amino acids, one or more non-amino acid diacids, or non-acid containing spacers, or a combination thereof.

10. The compound of claim 1, wherein $X^1$ and $X^2$ are each independently derived from glycine, glycine-glycine, aspartic acid, glycine-aspartic acid, or cysteine-succinic acid.

11. The compound of claim 1, wherein $X^1$ is derived from glycine-glycine and $X^2$ is derived from aspartic acid.

12. The compound of claim 1, wherein $X^1$ and $X^2$ each derived from glycine-aspartic acid.

13. The compound of claim 1 which crosslinks residues of the protein to be modified that are separated from about 20 Å to about 100 Å.

14. The compound of claim 1 which crosslinks residues of the protein to be modified that are separated by about 20 Å to about 30 Å.

15. A compound selected from the group consisting of:

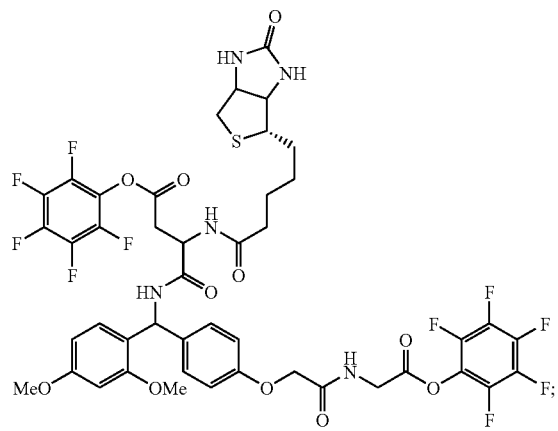

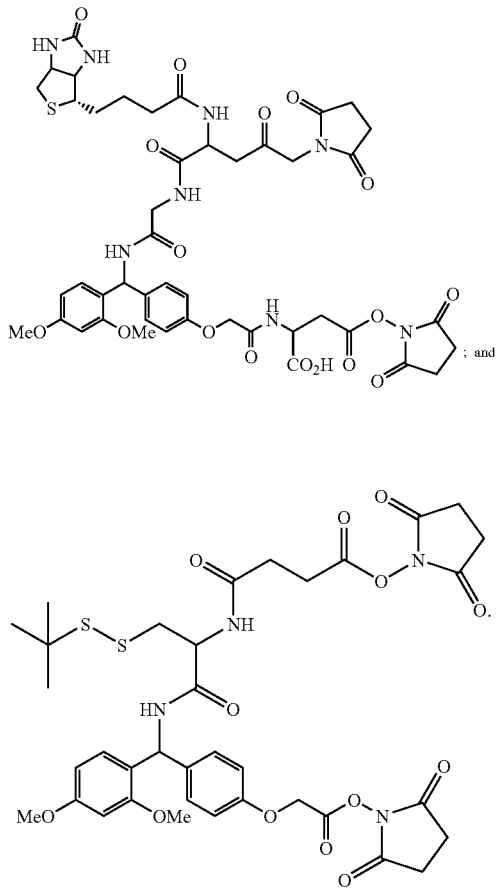

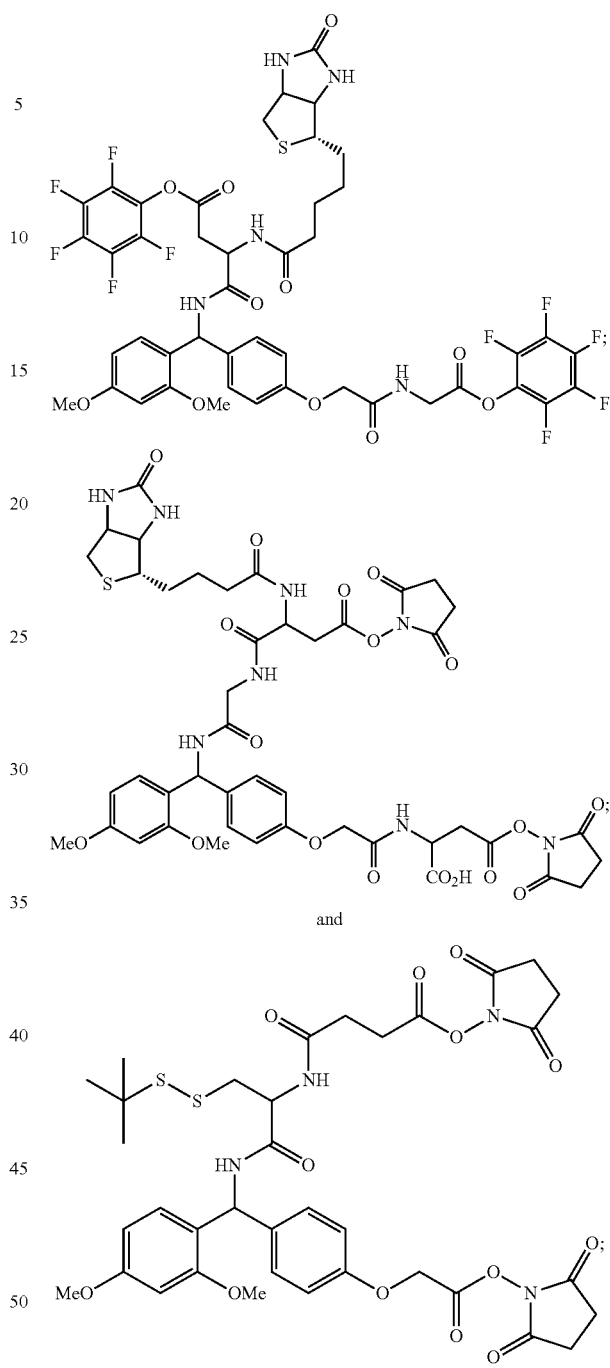

16. A method to identify complexed proteins and the location of proximal lysine residues in a sample containing said proteins which method comprises:
    treating said sample with the crosslinker compound of Formula (I) of claim 1 to obtain a mixture of crosslinker-modified proteins;
    treating the mixture of crosslinker-modified proteins with a protease to obtain digested crosslinker-modified peptides;
    purifying the digested crosslinker-modified peptides to separate crosslinker-modified peptides from unmodified peptides; and
    obtaining mass spectra of the crosslinker-modified peptides as well as mass spectra of fragmentation products derived from the crosslinker-modified peptides.

17. A method to identify complexed proteins and the location of proximal lysine residues in a sample containing said proteins which method comprises:
    treating said sample with a compound selected from the group consisting of:

to obtain a mixture of crosslinker-modified proteins;
treating the mixture of crosslinker-modified proteins with a protease to obtain digested crosslinker-modified peptides;
purifying the digested crosslinker-modified peptides to separate crosslinker-modified peptides from unmodified peptides; and
obtaining mass spectra of the crosslinker-modified peptides as well as mass spectra of fragmentation products derived from the crosslinker-modified peptides.

* * * * *